US010613182B2

(12) United States Patent
Le Bihan

(10) Patent No.: US 10,613,182 B2
(45) Date of Patent: Apr. 7, 2020

(54) MRI METHOD TO QUANTIFY IRON AMOUNT IN TISSUES USING DIFFUSION MAGNETIC RESONANCE IMAGING

(71) Applicant: COMMISSARIAT A L'ENERGIE ATOMIQUE ET AUX ENERGIES ALTERNATIVES, Paris (FR)

(72) Inventor: Denis Le Bihan, Saint Nom La Breteche (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 586 days.

(21) Appl. No.: 15/316,474

(22) PCT Filed: Jun. 9, 2015

(86) PCT No.: PCT/IB2015/054350
§ 371 (c)(1),
(2) Date: Dec. 5, 2016

(87) PCT Pub. No.: WO2015/189769
PCT Pub. Date: Dec. 17, 2015

(65) Prior Publication Data
US 2017/0146629 A1 May 25, 2017

(30) Foreign Application Priority Data
Jun. 12, 2014 (EP) .................................... 14305887

(51) Int. Cl.
*G01R 33/563* (2006.01)
*A61B 5/055* (2006.01)
(Continued)

(52) U.S. Cl.
CPC ........ *G01R 33/56341* (2013.01); *A61B 5/055* (2013.01); *G01R 33/5608* (2013.01); *G01R 33/5616* (2013.01)

(58) Field of Classification Search
CPC .......... G01R 33/56341; G01R 33/5608; G01R 33/5616; A61B 5/055
(Continued)

(56) References Cited

U.S. PATENT DOCUMENTS 5,322,682 A * 6/1994 Bartzokis ............... A61B 5/055
 324/300
9,076,196 B2 * 7/2015 McAuley .............. G06T 7/0012
(Continued)

OTHER PUBLICATIONS

Deistung, A., et al., "Toward In Vivo Histology: A Comparison of Quantitative Susceptibility Mapping (QSM) With Magnitude-, Phase-, and $R_2^*$-Imaging at Ultra-High Magnetic Field Strength," NeuroImage 65:299-314, Oct. 2012.
(Continued)

*Primary Examiner* — Patrick Assouad
*Assistant Examiner* — Demetrius R Pretlow
(74) *Attorney, Agent, or Firm* — Christensen O'Connor Johnson Kindness PLLC

(57) ABSTRACT

A method to quantify and map iron deposits in the brain with diffusion-weighted magnetic resonance imaging (MRI) is based on the differential sensitivity of mono-polar (MPG) gradient pulse diffusion sequences and bipolar (BPG) sequences on the local magnetic field gradients induced by iron deposits and their cross-term with the diffusion-encoding gradients. The method comprises the steps of acquiring (12, 14) first MRI images and second MRI of a Region Of Interest by using MPG and BPG sequences, providing (16) an attenuation model of the diffusion MRI attenuated signal representative of the observed tissue, estimating (18, 20) a first apparent diffusion coefficient ADCMPG and a second
(Continued)

apparent diffusion coefficient ADCBPG by fitting the MRI images with the attenuation model, calculating (22) a an iron induced local gradient factor $\xi_{Fe}$ as (Formula I) (I), and determining (24) the concentration [Fe] and/or the amount of iron stored in the local zone of the tissue from the calculated iron induced local gradient factor $\xi_{Fe}$. An apparatus is configured for implementing such a method.

19 Claims, 7 Drawing Sheets

(51) Int. Cl.
    *G01R 33/56*     (2006.01)
    *G01R 33/561*     (2006.01)
(58) Field of Classification Search
    USPC .......................................................... 324/309
    See application file for complete search history.

(56) References Cited

U.S. PATENT DOCUMENTS

| | | | | |
|---|---|---|---|---|
| 2004/0071324 | A1* | 4/2004 | Norris | G01R 33/56509 |
| | | | | 382/128 |
| 2004/0102692 | A1* | 5/2004 | Schenck | A61B 5/055 |
| | | | | 600/410 |
| 2005/0020904 | A1* | 1/2005 | Cline | A61B 5/055 |
| | | | | 600/410 |
| 2009/0299172 | A1 | 12/2009 | Corot et al. | |
| 2010/0284928 | A1* | 11/2010 | Raman | A61B 5/055 |
| | | | | 424/9.3 |
| 2011/0280460 | A1 | 11/2011 | McAuley et al. | |
| 2013/0208969 | A1* | 8/2013 | Bashir | G06T 7/0012 |
| | | | | 382/131 |
| 2014/0126795 | A1* | 5/2014 | Zhong | G01R 33/4828 |
| | | | | 382/131 |
| 2014/0266195 | A1* | 9/2014 | Levin | G01R 33/56509 |
| | | | | 324/309 |
| 2014/0330106 | A1* | 11/2014 | Banerjee | G01R 33/4828 |
| | | | | 600/410 |
| 2016/0025831 | A1* | 1/2016 | Tunnicliffe | A61B 5/055 |
| | | | | 324/322 |
| 2016/0054410 | A1* | 2/2016 | Schenck | A61B 5/055 |
| | | | | 600/410 |

OTHER PUBLICATIONS

Does, M.D., et al., "In Vivo Measurement of ADC Change Due to Intravascular Susceptibility Variation," Magnetic Resonance in Medicine 41(2):236-240, Jan. 1999.
Ge, Y., et al., "Quantitative Assessment of Iron Accumulation in the Deep Gray Matter of Multiple Sclerosis by Magnetic Field Correlation Imaging," AJNR, American Journal of Neuroradiology 28(9):1639-1644, Sep. 2007.
Hong, X., and W.T. Dixon, "Measuring Diffusion in Inhomogeneous Systems in Imaging Mode Using Antisymmetric Sensitizing Gradients," Journal of Magnetic Resonance 99(3):561-570, Oct. 1992.
International Search Report and Written Opinion dated Sep. 14, 2015, issued in corresponding International Application No. PCT/IB2015/054350, filed Jun. 9, 2015, 17 pages.
Kiselev, V.G., "Effect of Magnetic Field Gradients Induced by Microvasculature on NMR Measurements of Molecular Self-Diffusion in Biological Tissues," Journal of Magnetic Resonance 170(2):228-235, Jul. 2004.
Le Bihan, D., et al., "Brain Tissue Water Comes in Two Pools: Evidence From Diffusion and R2' Measurements With USPIOs in Non Human Primates," NeuroImage 62(1):9-16, May, 2012.
Reese, T.G., et al., "Reduction of Eddy-Current-Induced Distortion in Diffusion MRI Using a Twice-Refocused Spin Echo," Magnetic Resonance in Medicine 49(1):177-182, Jan. 2003.
Sedlacik, J., et al., "Reversible, Irreversible and Effective Transverse Relaxation Rates in Normal Aging Brain at 3 T," NeuroImage 84:1032-1041, Sep. 2013.
Sener, R.N., "Echo-Planar and Gradient-Echo Diffusion MRI of Normal Brain Iron in the Globus Pallidus," Journal of Clinical Imaging 26(6):371-374, Feb. 2002.
Zhong, J., et al., "Effects of Susceptibility Variations on NMR Measurements of Diffusion," Journal of Magnetic Resonance 95(2):267-280, Nov. 1991.

\* cited by examiner

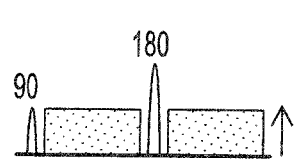
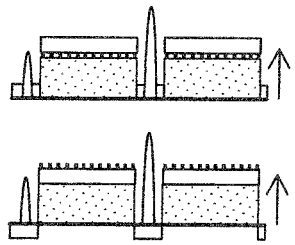
Fig. 2A
Fig. 2B
Fig. 2C
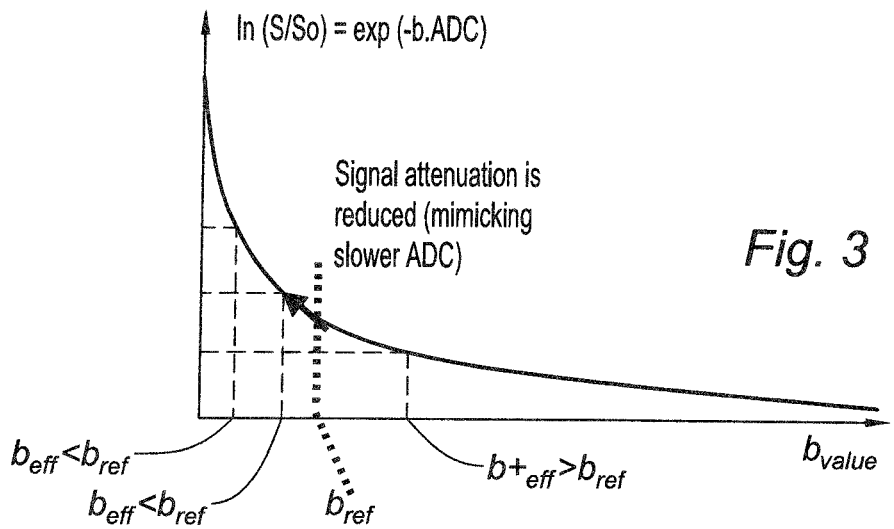
Fig. 3
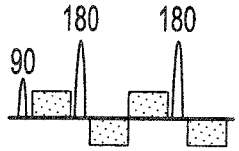
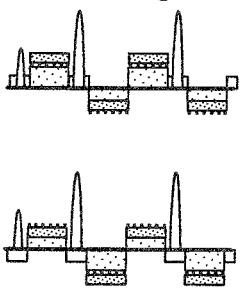
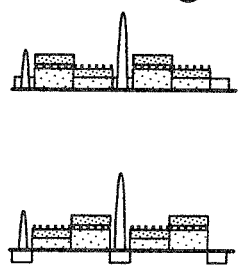
Fig. 4A
Fig. 4B
Fig. 4C
Fig. 4D
Fig. 4E

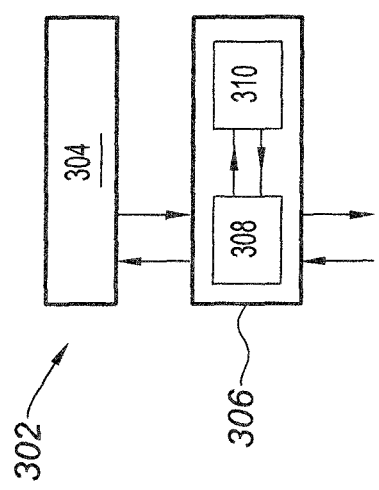
Fig. 7
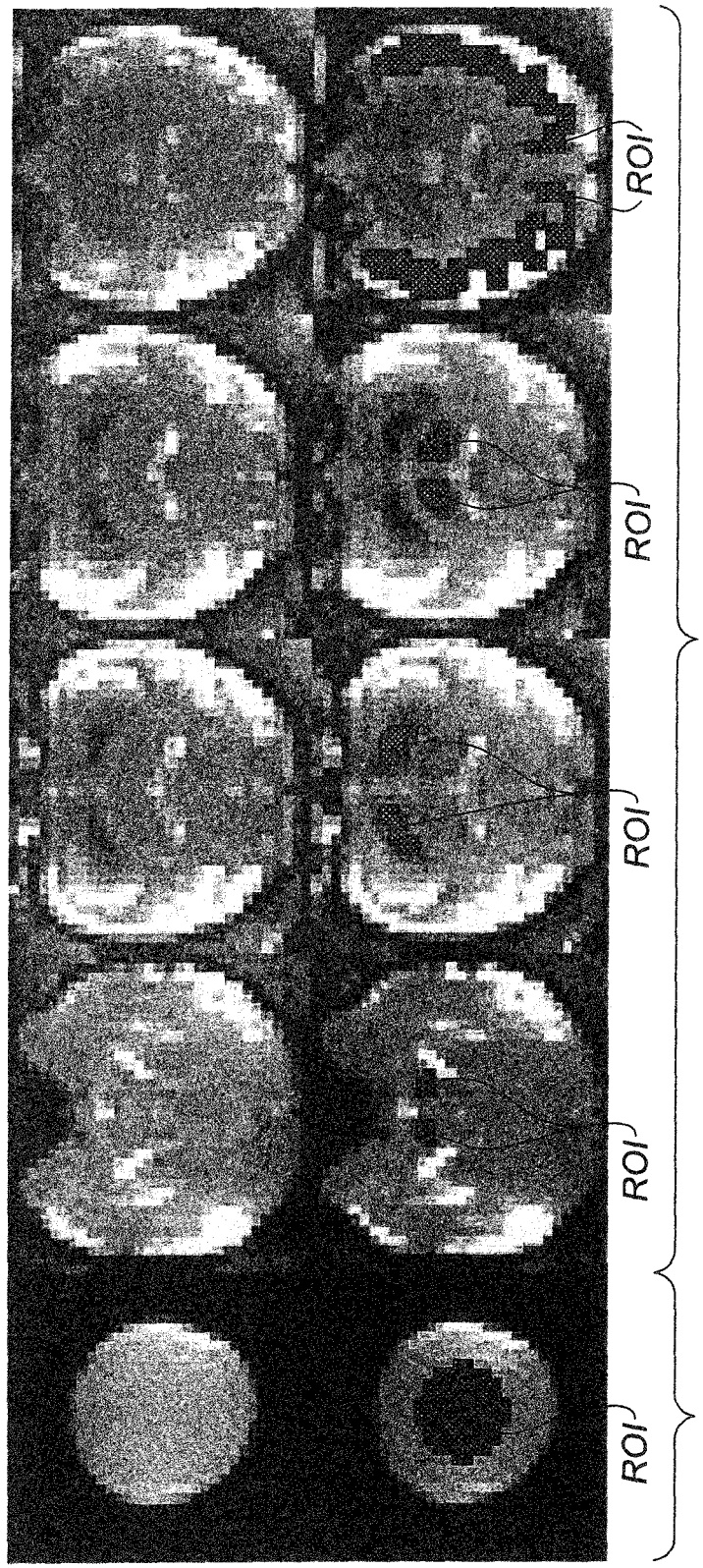
Fig. 8b
Fig. 8a

MRI METHOD TO QUANTIFY IRON AMOUNT IN TISSUES USING DIFFUSION MAGNETIC RESONANCE IMAGING

The invention relates to the field of the use of magnetic resonance imaging in medicine. The invention concerns a method to measure iron stores in tissues of various organs, and in particular to quantitatively and specifically measure in vivo the concentration or the quantity of iron in a tissue. The invention also concerns an apparatus to carry out such a method of measurement.

Iron excess has been linked to many illnesses, such as chronic liver disease, arthritis, cardiovascular diseases, cancer, etc. Effects can be severe in patients suffering from iron-loading disorders, such as hemochromatosis, thalassemia, sickle cell disease, etc. Iron deposits in the brain, especially basal ganglia, occur naturally over years, but might lead to severe neurodegenerative disorders like Parkinson's disease (Griffiths, et al., 1993 and 1999; Berg D, et al., 2006). Reliable assessment of iron stores usually requires analysis of liver biopsy specimen, an invasive procedure which provides global information on body iron overload, but not in specific tissues. Hence there is a need for non-invasive methods which could estimate iron load in tissues. Iron deposits get transiently magnetized (paramagnetic magnetization) in the magnetic field of Magnetic Resonance Imaging (MRI) scanners and are responsible for local changes in Bulk Magnetic Susceptibility (BMS) which, in turn, often result in a signal loss in the images acquired with gradient-echo sequences due to intravoxel dephasing and an increase R2* relaxivity (Milton, et al., 1991; Antonini, et al., 1993; Schenker, et al., 1993; Gorell, et al., 1995; Brass, et al., 2006). Iron detection/quantification methods have been developed based on this effect (Haacke, et al., 2005; Hardy, et al., 2005; Wallis, et al. 2008; Péran, et al., 2009; Aquino, et al., 2009; Deistung, et al., 2013; Sedlacik, et al., 2014) and applied to investigate iron biological effects in the brain of normal aging subjects (Aquino, et al. 2009; Sedlacik, et al., 2014) and in patients with neurodegenerative diseases, such as Parkinson's disease (Graham et al. 2000; Wallis et al., 2008; Perm, et al., 2009). Iron related BMS effects have also been investigated in the brain of patients with multiple sclerosis using Magnetic Field Correlation (MTC) Imaging (Ge Y et al. AJNR 28:1639-1644, 2007) but the relationship between iron content and MTC is not straightforward and no actual quantification as been reported.

Those phase shift and T2* approaches are currently been used to evaluate iron load in the liver (Gandon et al. 2004; St. Pierre et al. 2005).

However, this method of quantification suffers from well known pitfalls, especially as iron induced BMS effects are not the unique source of signal phase shifts and R2* changes in tissues (Deistung, et al., 2013; Sedlacik, et al., 2014). More specificity can be obtained by combining measurements obtained at two different field strengths, but this is obviously impractical in clinical practice. The ideal method should detect/quantify iron deposits on a local basis in tissues, be easy to implement and not require long acquisition time for patients, as well as provide accurate and reproducible results.

On the other hand, iron induced BMS effects are also responsible for the presence of small local magnetic field gradients. In the context of diffusion MRI such local gradients produce non-negligible cross-terms with the programmed gradient pulses inserted for diffusion encoding, resulting in an underestimation of the measured Apparent Diffusion Coefficient (ADC), as evidenced with the decrease ADC observed after administration of ultra-small iron oxide particles (USPIO) in the liver (Zhong, et al., 1991; Does, et al., 1999) or in the presence of iron in brain basal ganglia (Sener R. N. J. Clinical Imaging, 26:371-374, 2002).

Contrary to the R2* effect which cannot be reversed, this effect on the ADC can be eliminated when using diffusion MRI sequences immune to effects of local magnetic field gradients, for instance using an antisymmetric diffusion-sensitizing gradient pulse sequence (Hong X et al. JMR 99, 561-570, 1992). Such a MRI sequence made of "bipolar" gradient pulses (BPG) instead of the usual "monopolar" gradient pulses (MPG) (Zhong, et al., 1998; Reese et al., 2003).

The effect of iron on the ADC has been considered as an artifact and the bipolar sequence as a way to remove this artifact to get clean diffusion MRI measurements. For instance the BPG sequence has been shown to provide correct estimates of water diffusion parameters in the brain of primates despite the presence of iron-containing tracers which had been injected in the blood stream, while the parameter estimates were erroneous when using the MPG sequence (Le Bihan et al. NeuroImage 62:9-16, 2012). Oppositely, this artifactual effect of iron on the ADC obtained using a MPG sequence has been proposed to enhance the image contrast obtained after injection of iron-containing contrast agents (Corot et al. Patent US2009/0299172). However, all those studies felt short of suggesting that those "erroneous" parameter estimations might be exploited to provide iron content in a quantitative manner. More generally, it is has never been shown or even suggested that the comparison of the ADCs obtained with the MPG and BPG sequences could be used to actively retrieve quantitative information of iron content, despite the effect of iron on the ADC measured with the MPG sequence has been known as early as 1991. To the contrary, the invention exploits the specific features of the monopolar and bipolar pulsed gradient sequences to quantitatively assess iron deposits in tissues To that end, the invention relates to a first main embodiment of method for quantifying iron deposits in tissues using diffusion-weighted Magnetic Resonance Imaging (MRI) with a high accuracy, comprising the steps of:

acquiring a first series of MRI images of a Field Of View (FOV) of a biological tissue by using a MonoPolar pulse-diffusion Gradient (MPG) sequence as a MonoPolar pulse-diffusion Gradient Spin-Echo sequence (PGSE), and by varying a programmed gradient attenuation factor $\underline{b}$ over a first plurality of values, the programmed gradient attenuation factor depending only on the set of the diffusion gradient pulses of the first sequence;

acquiring a second series of MRI images of the same Field of View FOV of the biological tissue by using as a BiPolar pulse-diffusion Gradient (BPG) sequence a pulse-diffusion gradient spin echo sequence free of cross-terms with local background gradients having a similar diffusion time as the MPG sequence, and by varying a programmed gradient attenuation factor $\underline{b}$ over a second plurality of values, the programmed gradient attenuation factor depending only on the set of the diffusion gradient pulses of the BPG sequence;

providing an attenuation model of the diffusion MRI attenuated signal $S/S_0$ representative of the observed tissue expressed as a model function f(x) depending on a variable $\underline{x}$ equal to the product of an apparent model diffusion coefficient ADC and the programmed gradient attenuation factor $\underline{b}$ used;

on a one-per-one voxel basis or on a predetermined Region Of Interest (ROI) including a set of voxels, estimating a first apparent diffusion coefficient $ADC_{MPG}$ by fitting the MRI images acquired by using the MPG sequence and the first plurality of programmed gradient attenuation factors $\underline{b}$ with the model function f(b.ADC);

estimating a second apparent diffusion coefficient $ADC_{BPG}$ by fitting the MRI images acquired by using the BPG sequence and the second plurality of programmed gradient attenuation factors $\underline{b}$ with the model function f(b.ADC);

calculating an iron induced local gradient factor $\xi_{Fe}$ from the estimated values of the first apparent diffusion coefficient $ADC_{MPG}$ and the second apparent diffusion coefficient $ADC_{BPG}$ through the relationship:

$$\xi_{Fe} = 1 - \frac{ADC_{MPG}}{ADC_{BPG}}.$$

According to specific embodiments, the first main embodiment of the method for quantifying iron deposits in tissues comprises one or more of the following features:

- the concentration [Fe] and/or the amount of iron stored in the ROI or each voxel of the tissue is determined from the calculated iron induced local gradient factor $\xi_{Fe}$ through a predetermined monotonic conversion function $g^{-1}(\xi_{Fe})$;
- the conversion function $g^{-1}(\xi_{Fe})$ is a linear function or a portion of a quadratic function;
- the BPG sequence is a twice refocused spin-echo sequence allowing any diffusion gradients lengths such that the time between the two refocusing pulses is equal to TE/2, and the phasing and re-phasing due to the diffusion gradients are equal, TE designating the echo time;
- the mono-polar Pulse-diffusion field Gradient Spin-Echo sequence is a singly-refocused Stejkal-Tanner spin-echo sequence;
- the method comprises further a step of determining a two-dimensional map or a three-dimensional map of the iron induced iron induced local gradient factor $\xi_{Fe}$ or the iron concentration [Fe] or iron quantities deposited in the observed tissue when the estimation steps are carried out on a one per one voxel basis;
- the model function f(x) is mono-exponential and is expressed by a first model function $f_1(x)$ as:

$f_1(b.\text{ADC})) = \exp(-b.\text{ADC})$;

- the model function f(x) is a Kurtosis function, and is expressed by a second model function $f_2(x)$ as:

$f_2(b.\text{ADC}) = \exp(-b.\text{ADC} + K.(b.\text{ADC})^2/6)$ where K is the kurtosis related to a $4^{th}$ moment of the molecular displacement in a narrow gradient pulse regime;
- the observed tissue is a tissue of the set consisting of the brain tissues, liver tissues, heart joints tissues;
- the estimation of the first apparent diffusion coefficient $ADC_{MPG}$ and the estimation of the second apparent diffusion coefficient $ADC_{BPG}$ are carried out by comparing the raw MRI signal data with a database of simulated signals built once-for-all using an exhaustive set of parameters combinations, the parameters being those of the model function f(x) and including at least the programmed gradient attenuation factor $\underline{b}$ and the apparent model diffusion coefficient ADC.

The invention also relates to a second main embodiment of method for quantifying iron deposits in tissues using diffusion-weighted Magnetic Resonance Imaging (MRI) with a high accuracy, comprising the steps of:

acquiring a first series of MRI images of a Field Of View (FOV) of a biological tissue by using a MonoPolar pulse-diffusion Gradient (MPG) sequence as a MonoPolar pulse-diffusion Gradient Spin-Echo sequence (PGSE), and by varying a programmed gradient attenuation factor $\underline{b}$ over a first plurality of values, the programmed gradient attenuation factor depending only on the set of the diffusion gradient pulses of the first sequence;

acquiring a second series of MRI images of the same Field of View FOV of the biological tissue by using as a BiPolar pulse-diffusion Gradient (BPG) sequence a cross-term-free pulse-diffusion gradient spin echo sequence having a similar diffusion time as the MPG sequence, and by varying a programmed gradient attenuation factor $\underline{b}$ over a second plurality of values, the programmed gradient attenuation factor depending only on the set of the diffusion gradient pulses of the BPG sequence;

providing an attenuation model of the diffusion MRI attenuated signal $S/S_0$ representative of the observed tissue, $f_{n,j}(b.\text{ADC}_1, \ldots, b.\text{ADC}_n)$ which can be expressed as:

$$f_{n,j}(b.ADC_1, \ldots, b.ADC_n) = \sum_{i=1}^{n} r_i \cdot f_j(b.ADC_i),$$

wherein n designates the total number of the diffusing water pools and is higher than or equal to 2, i is an index assigned to a diffusing water pool varying from 1 to n, j is an integer equal to 1 or 2 with $f_1(b.\text{ADC}_i)$ being the mono-exponential function as defined in claim 7 and $f_2(b.\text{ADC}_i)$ being the Kurtosis function as defined here above, $ADC_1, \ldots, ADC$, are the model apparent model diffusion coefficients corresponding to different diffusing water pools, and $r_1, \ldots, r_n$ are the relative fractions corresponding to the different diffusing water pools with $$\sum_{i=1}^{n} r_i = 1;$$

on a one-per-one voxel basis or on a predetermined Region Of Interest (ROI) including a set of voxels, estimating jointly a first set of apparent diffusion coefficient $ADC_{i,MPG}$ by fitting the MRI images acquired by using the MPG sequence and the first plurality of programmed gradient attenuation factors $\underline{b}$ with the model function $f_{n,j}(b.\text{ADC}_1, \ldots, b.\text{ADC}_n)$;

estimating jointly a second set of apparent diffusion coefficient $ADC_{i,BPG}$ by fitting the MRI images acquired by using the BPG sequence and the second plurality of programmed gradient attenuation factors $\underline{b}$ with the model function $f_{n,j}(b.\text{ADC}_1, \ldots, b.\text{ADC}_n)$;

calculating a first apparent diffusion coefficient $ADC_{MPG}$ and a second apparent diffusion coefficient $ADC_{BPG}$ according to the relationships:

$$ADC_{MPG} = \sum_{i=1}^{n} r_i \cdot ADC_{i,MPG}, \text{ and}$$

$$ADC_{BPG} = \sum_{i=1}^{n} r_i \cdot ADC_{i,BPG},$$

calculating (22) a local gradient factor $\xi_{Fe}$ quantitatively reflecting the iron load from the calculated values of the first apparent diffusion coefficient $ADC_{MPG}$ and the second apparent diffusion coefficient $ADC_{BPG}$ through the relationship:

$$\xi_{Fe} = 1 - \frac{ADC_{MPG}}{ADC_{BPG}}.$$

According to specific embodiments, the second main embodiment of the method for quantifying iron deposits in tissues comprises one or more of the following features:

the concentration [Fe] and/or the amount of iron stored in the ROI or each voxel of the tissue is determined from the calculated iron induced local gradient factor $\xi_{Fe}$ through a predetermined monotonic conversion function $g^{-1}(\xi_{Fe})$.

The invention also relates to a first main embodiment of an apparatus for quantifying iron deposits in tissues comprising a magnetic resonance imaging scanner to operate diffusion-weighted magnetic resonance imaging with a high resolution and accuracy and a means for controlling the scanner and processing the imaging data acquired by the scanner;

the magnetic resonance imaging scanner being configured for generating a MPG sequence as a Mono-Polar Pulse-diffusion Gradient Spin-Echo (PGSE) sequence, and varying a programmed gradient attenuation factor $\underline{b}$ over a first plurality of values, the programmed gradient attenuation factor $\underline{b}$ depending only on the set of the gradient pulses; and generating a BPG sequence as a cross-term free pulse diffusion Gradient Spin-Echo sequence having a similar diffusion time as the MPG sequence, and varying a programmed gradient attenuation factor $\underline{b}$ over a second plurality of values; and acquiring a first series of MRI images of a Field Of View (FOV) of a biological tissue by using the MPG sequence for the different programmed gradient attenuation factor $\underline{b}$ values of the first plurality;

acquiring a second series of MRI images of the same Field Of View (FOV) of the biological tissue by using the BPG sequence for the different programmed gradient attenuation factor $\underline{b}$ values of the second plurality; and the means for controlling the scanner and processing the imaging data acquired by the scanner comprising a means for storing an attenuation model of the diffusion MRI attenuated signal $S/S_0$ representative of the observed tissue expressed as a model function f(x) depending on a variable $\underline{x}$ equal to the product of an apparent model diffusion coefficient ADC and the programmed gradient attenuation factor $\underline{b}$ used; and a processing means configured for, on a one-per-one voxel basis or on a predetermined Region Of Interest (ROI) including a set of voxels:

estimating a first apparent diffusion coefficient $ADC_{MPG}$ by fitting the MRI images acquired by using the MPG sequence and the first plurality of programmed gradient attenuation factors with the model function f(b.ADC);

estimating a second apparent diffusion coefficient $ADC_{BPG}$ by fitting the MRI images acquired by using the BPG sequence and the second plurality of programmed gradient attenuation factors, with the model function f(b.ADC);

calculating an iron induced local gradient factor $\xi_{Fe}$ from the estimated values of the first apparent diffusion coefficient $ADC_{MPG}$ and the second apparent diffusion coefficient $ADC_{BPG}$ through the relationship $$\xi_{Fe} = 1 - \frac{ADC_{MPG}}{ADC_{BPG}}.$$

According to specific embodiments, the first main embodiment of apparatus for quantifying iron deposits in tissues comprises one or more of the following features:

the means for storing a model stores at least one attenuation model function among a first model function $f_1(b.ADC)$, a second model function $f_2(b.ADC)$, the first model function $f_1(x)$ being mono-exponential and being expressed as:

$$f_1(b.\text{ADC})) = \exp(-b.\text{ADC});$$

the second model function $f_2(x)$ being a Kurtosis function and being expressed as:

$$f_2(b.\text{ADC}) = \exp(-b.\text{ADC} + K.(b.\text{ADC})^2/6)$$

where K is the kurtosis related to a $4^{th}$ moment of the molecular displacement in a narrow gradient pulse regime.

The invention also relates to a second main embodiment of an apparatus for quantifying iron deposits in tissues comprising a magnetic resonance imaging scanner to operate diffusion-weighted magnetic resonance imaging with a high resolution and accuracy and a means for controlling the scanner and processing the imaging data acquired by the scanner;

the magnetic resonance imaging scanner being configured for generating a MPG sequence as a Mono-Polar Pulse-diffusion Gradient Spin-Echo (PGSE) sequence, and varying a programmed gradient attenuation factor $\underline{b}$ over a first plurality of values, the programmed gradient attenuation factor $\underline{b}$ depending only on the set of the gradient pulses; and generating a BPG sequence as a cross-term free pulse diffusion Gradient Spin-Echo sequence having a similar diffusion time as the MPG sequence, and varying a programmed gradient attenuation factor $\underline{b}$ over a second plurality of values; and acquiring a first series of MRI images of a Field Of View (FOV) of a biological tissue by using the MPG sequence for the different programmed gradient attenuation factor $\underline{b}$ values of the first plurality;

acquiring a second series of MRI images of the same Field Of View (FOV) of the biological tissue by using the BPG sequence for the different programmed gradient attenuation factor $\underline{b}$ values of the second plurality; and the means for controlling the scanner and processing the imaging data acquired by the scanner comprising a means for storing an attenuation model of the diffusion MRI attenuated signal $S/S_0$ representative of the observed tissue, $f_{n,j}(b.ADC_1, \ldots, b.ADC_n)$ which is expressed as:

$$f_{n,j}(b.ADC_1, \ldots, b.ADC_n) = \sum_{i=1}^{n} r_i \cdot f_j(b.ADC_i),$$

wherein n designates the total number of the diffusing water pools and is higher than or equal to 2, i is an index assigned to a diffusing water pool varying from 1 to n, j is an integer equal to 1 or 2 with $f_1(b.ADC_i)$ being the mono-exponential function and $f_2(b.ADC_i)$ being the Kurtosis function as defined in claim 14, $ADC_1, \ldots, ADC_n$ are the model apparent model diffusion coefficients corresponding to different diffusing water pools, and $r_1, \ldots, r_n$ are relative fractions corresponding to different pools with $$\sum_{i=1}^{n} r_i = 1;$$

and a processing means configured for, on a one-per-one voxel basis or on a predetermined Region Of Interest (ROI) including a set of voxels:

estimating jointly a first set of apparent diffusion coefficient $ADC_{i,MPG}$ by fitting the MRI images acquired by using the MPG sequence and the first plurality of programmed gradient attenuation factors $\underline{b}$ with the model function $f_{n,j}$ $(b.ADC_1, \ldots, b.ADC_n)$;

estimating jointly a second set of apparent diffusion coefficient $ADC_{i,BPG}$ by fitting the MRI images acquired by using the BPG sequence and the second plurality of programmed gradient attenuation factors $\underline{b}$ with the model function $f_{n,j}(b.ADC_1, \ldots, b.ADC_n)$;

calculating a first apparent diffusion coefficient $ADC_{MPG}$ and a second apparent diffusion coefficient $ADC_{BPG}$ according to the relationships:

$$ADC_{MPG} = \sum_{i=1}^{n} r_i \cdot ADC_{i,MPG}, \text{ and}$$

$$ADC_{BPG} = \sum_{i=1}^{n} r_i \cdot ADC_{i,BPG};$$

calculating an iron induced local gradient factor $\xi_{Fe}$ from the estimated values of the first apparent diffusion coefficient $ADC_{MPG}$ and the second apparent diffusion coefficient $ADC_{BPG}$ through the relationship $$\xi_{Fe} = 1 - \frac{ADC_{MPG}}{ADC_{BPG}}.$$

According to specific embodiments, the first main embodiment and the second main embodiment of apparatus for quantifying iron deposits in tissues comprise one or more of the following features:

the concentration [Fe] and/or the amount of iron stored in the ROI or each voxel of the tissue is determined from the calculated iron induced local gradient factor $\xi_{Fe}$ through a predetermined monotonic conversion function $g^{-1}(\xi_{Fe})$.

the processing means is configured for determining a two-dimensional map or a three-dimensional map of the iron induced local gradient factor $\xi_{Fe}$ or the iron concentration [Fe] or iron quantities deposited in the observed tissue when the estimation steps are carried out on a one per one voxel basis.

The invention also relates to computer software comprising a set of instructions stored in the apparatus as defined here above and configured to carry out the steps of the method as defined in any of claims here above when they are executed by the apparatus.

The invention also relates to computer software comprising a set of instructions stored in a stand-alone computer configured to carry out the steps of the method as defined here above and related to the processing of the MRI images in order to determine an iron induced local gradient factor $\xi_{Fe}$ and/or a concentration [Fe] and/or an amount of iron stored in a ROI or a voxel of a biological tissue.

The invention will be better understood from a reading of the description of several embodiments below, given purely by way of example and with reference to the drawings, in which:

FIG. 1 is an flow chart of a method according to a first main embodiment of the invention for quantifying iron deposits in tissues;

FIGS. 2A, 2B, 2C are respectively a first diagram of an example of a programmed mono-polar PGSE sequence, a second schematic diagram of a first extreme case configuration of all the superposed actual gradients corresponding to the case wherein the effective $b^-_{\textit{eff}}$ value is lower than the reference (programmed) b value, a third schematic diagram of a second extreme case configuration of all the superposed actual gradients corresponding to the case wherein the effective $b^+_{\textit{eff}}$ value is higher than the reference programmed $\underline{b}$ value;

FIG. 3 is a view showing the effect of the non linear nature of the diffusion signal attenuation profile and random distribution of the local magnetic field gradients on the overall effective $\underline{b}$ value $b_{\textit{eff}}$;

FIG. 4A, 4B, 4C, 4D, 4E are respectively a first diagram of an example of a programmed bipolar PGSE sequence, a second schematic diagram of a first extreme case configuration of all the superposed actual gradients corresponding to the case wherein the applied gradients, the local gradients and the background gradients are collinear, a third schematic diagram equivalent to the second schematic diagram, a fourth schematic diagram of a second extreme case configuration of all the superposed actual gradients corresponding to the case wherein the applied gradients, the local gradients and the background gradients are anti-linear;

FIG. 7 is a view of an apparatus according to the invention implementing the method as described in FIGS. 1 and 5;

Figure 9:
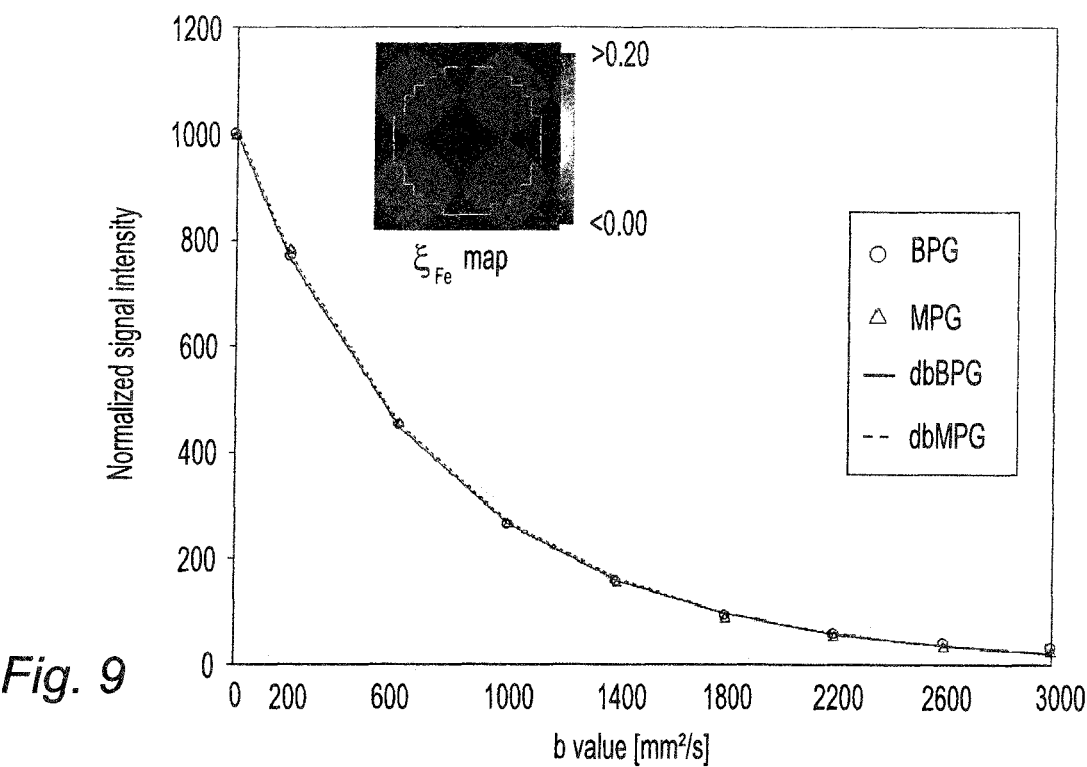

FIGS. 8*a* and 8*b* are respectively views of the ROI locations on a phantom and in a monkey B for the Substantia Nigra, the Globus Pallidus, the thalamus and the cortex;

FIG. 9 is a comparative view of the evolution of normalized signal intensity versus the $\underline{b}$ value for the signals measured in the ROIs at the phantom study corresponding to the use of a MPG sequence and a BPG sequence, and for the corresponding selected simulated signals dbBPG and dbMPG obtained from the adaptive database signals, and a view of the $\xi_{Fe}$ map calculated from $ADC_{MPG}$ and $ADC_{BPG}$ showing no distribution of the iron.

Figure 11:
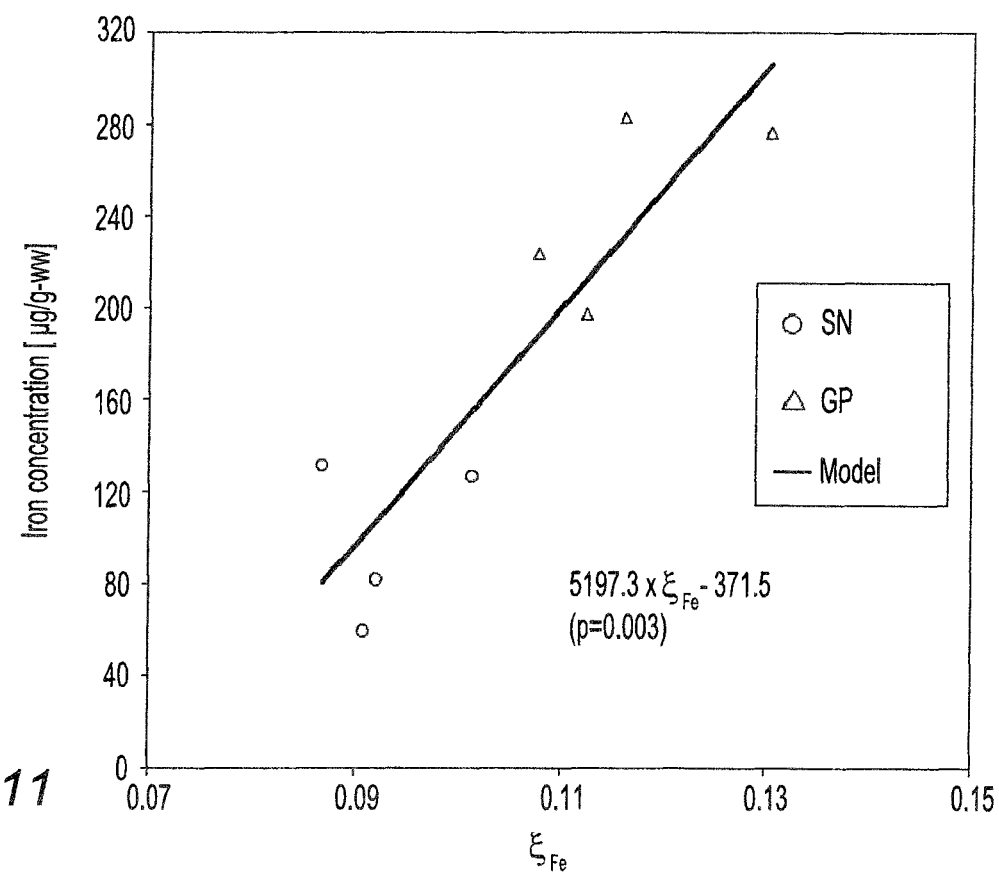
Figure 10:
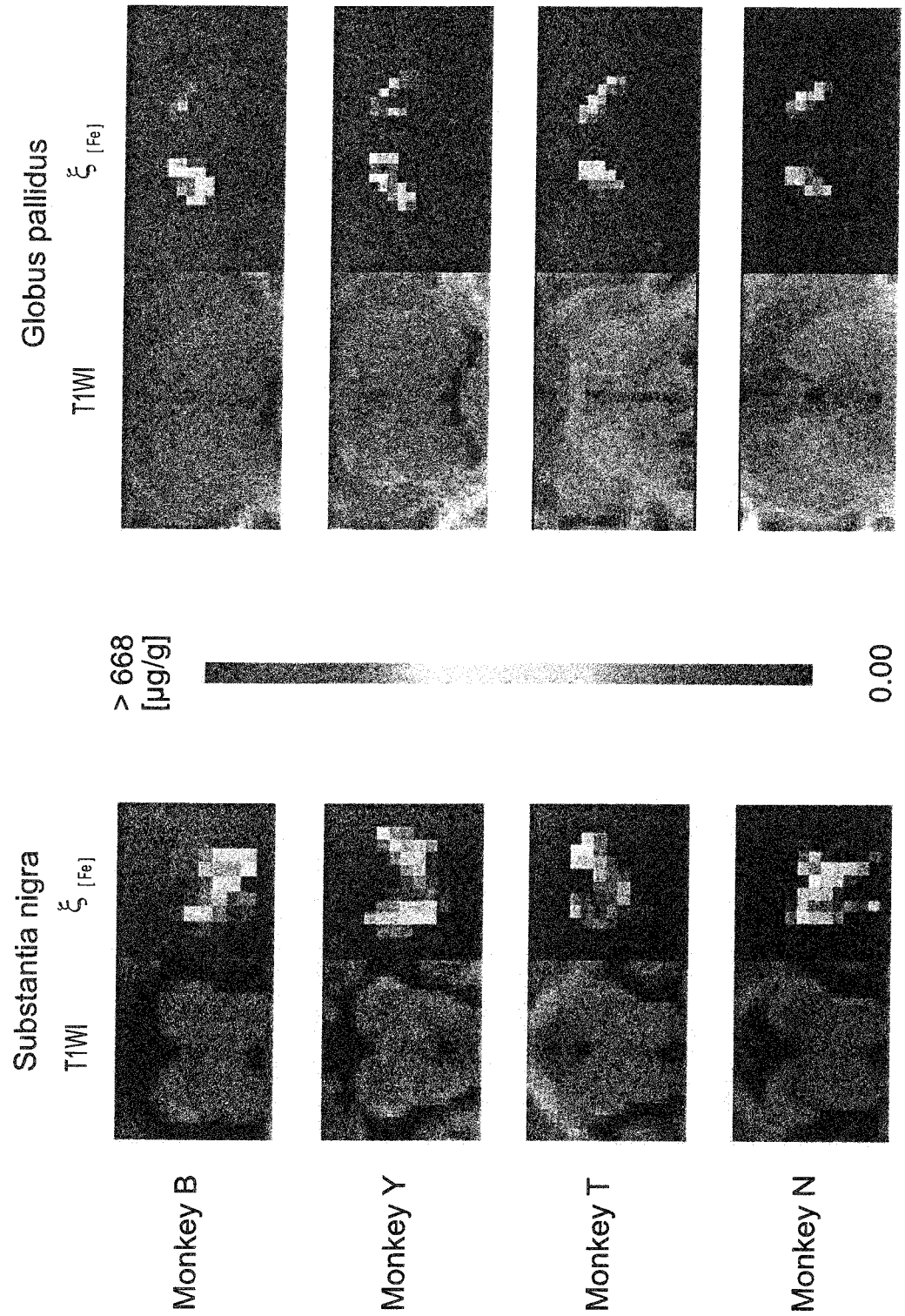

FIG. 10 is a comparative set of anatomical T1-weighted images and $\xi_{Fe}$ maps including the Substantia Nigra and Globus Pallidus in four monkeys B, Y, T, N, the regions with high $\xi_{Fe}$ values indicating a high iron concentration;

FIG. 11 illustrates the linear relationship between the iron induced local gradient factor $\xi_{Fe}$ determined by the method of the invention and the estimated iron concentration derived from experimental data from Hardy P. A. et al.

Figure 1:
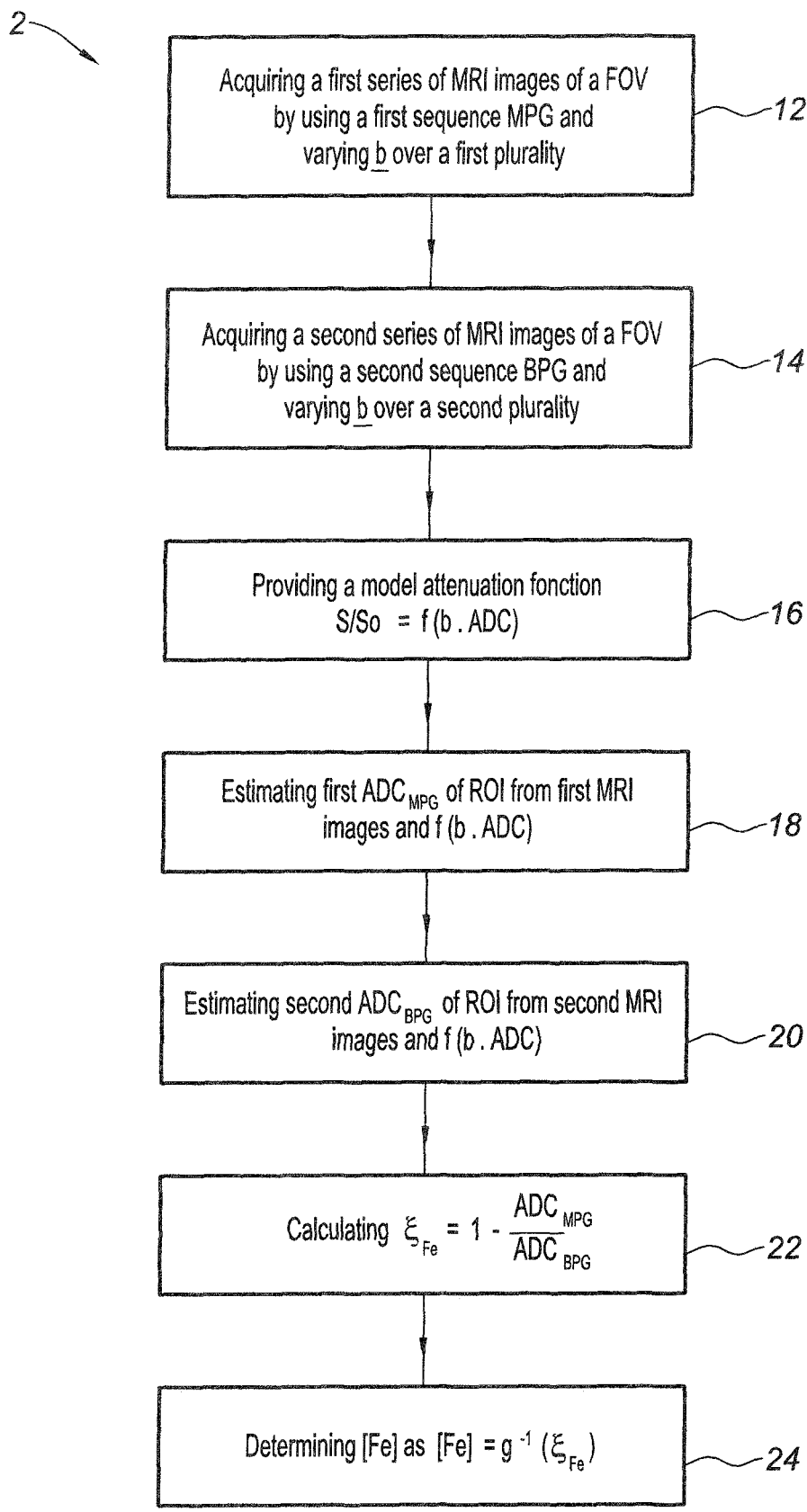

As shown in FIG. 1 and according to a first main embodiment of the invention, a method for quantifying iron deposits in tissues using diffusion-weighted magnetic resonance imaging comprises a set 2 of steps 12, 14, 16, 18, 20, 22 and 24.

In a first step 12, a first series of MRI images of a Field Of View (FOV) of a biological tissue are acquired by using as a first sequence a mono-polar Pulse-diffusion Gradient Spin-Echo (PGSE) sequence, also designated as MPG (Mono-Polar Gradient) sequence. This sequence is sensitive to the local background magnetic field gradients induced by iron through cross-terms between those gradients and the pulsed gradient. The images are acquired by varying a gradient attenuation factor b over a first plurality of values, the attenuation factor depending only on the set of the gradient pulses.

In a second step 14, a second series of MRI images of the same Field Of View (FOV) of the biological tissue are acquired by using here a bipolar Pulse-diffusion Gradient Spin-Echo sequence, also designated as BPG (Bi-Polar Gradient) sequence. The images are acquired by varying a gradient attenuation factor b over a second plurality of values that here as a particular case will be the same as ones of the first plurality. The second step 14 can be executed after or before the first step 12. The acquisitions of the MRI images of the first and second series can be even interleaved.

As BPG sequence used in the step 14, the so-called "cross-term-free pulse diffusion gradient spin echo sequence", described in the paper of Hong X. et al., entitled "Measuring Diffusion in Imaging Mode Using Antisymmetric Sensitizing Gradients", Journal of Magnetic Resonance, 99, 561-570, (1992), can be used. Such a BPG sequence has its diffusion-sensitizing gradients and RF pulses arranged so that the cross terms between the imaging gradient, the local gradient, the sensitizing gradient are equal to zero at the echo time TE period.

In a third step 16, an attenuation model of the diffusion MRI attenuated signal $S/S_0$, representative of the observed tissue, is provided after the first and second steps 12, 14. Such MRI attenuation model is expressed as a model function f(x) depending on a variable x equal to the product of an apparent diffusion coefficient ADC and the programmed gradient attenuation factor b used.

As a variant, the attenuation model can be provided before the first and second steps 12, 14.

Then, after executing the first, second, and third steps 12, 14, 16, on a one per one voxel basis or on a predetermined Region Of Interest (ROI) defined as a set of voxels, fourth, fifth, sixth and seventh steps, respectively referenced as 18, 20, 22, 24 and as described here below are executed.

In the fourth step 18, a first apparent diffusion coefficient $ADC_{MPG}$ is estimated from the MRI images acquired by using the MPG sequence and the programmed gradient attenuation factors b of the MPG sequence, and from the model function $f(b.ADC_{MPG})$.

In the fifth step 20, a second apparent diffusion coefficient $ADC_{BPG}$ is estimated from the MRI images acquired by using the BPG sequence and the programmed gradient attenuation factors b of the BPG sequence, and from the model function $f(b.ADC_{BPG})$.

In the sixth step 22, the iron induced local gradient factor $\xi_{Fe}$ is calculated from the estimated values of the first apparent diffusion coefficient $ADC_{MPG}$ and the second apparent diffusion coefficient $ADC_{BPG}$ through the relation:

$$\xi_{Fe} = 1 - \frac{ADC_{MPG}}{ADC_{BPG}}. \quad \text{(equation \#1)}$$

The estimation and/or mapping of $\xi_{Fe}$ has already some practical value, giving a relative quantitative information on the iron content between tissues and/or status (e.g. normal or disease).

If an absolute quantification of iron is necessary, in the seventh step 24, the concentration [Fe] and/or the amount of iron stored in the ROI or each voxel of the tissue is determined through the calculated the iron induced local gradient factor $\xi_{Fe}$ through a predetermined conversion function $g^{-1}$ which is a monotonic function of the iron induced local gradient factor $\xi_{Fe}$, such that:

$$[Fe] = g^{-1}(\xi_{Fe}) \quad \text{(equation \#2)}.$$

This function can be determined from a physical model, but, preferably, empirically through a calibration method obtained using phantoms containing known quantities of iron.

Hence, in the presence of iron deposits a direct comparison of diffusion images acquired with the BPG and MPG sequences will reveal the presence of local field gradients, and, thus, the presence of iron. From the comparison of the diffusion images acquired with the BPG and MPG sequences and the use of a pertinent attenuation model of the diffusion MRI attenuated signal, it is therefore possible to determine accurately the quantity of iron deposited in a local zone of a tissue, especially a brain tissue.

According to the FIG. 2A, an example of a Mono-Polar Pulse-diffusion field Gradient Spin-Echo sequence is a single-refocused Stejkal-Tanner spin-echo sequence with one pair of Mono-Polar diffusion gradient pulses.

As a variant, the Mono-Polar Pulse-diffusion field Gradient Spin-Echo sequence is a multiple-refocused spin-echo sequence with at least two pairs of Mono-Polar diffusion gradient pulses.

Iron particles create local magnetic field gradients which cause a signal reduction in the tissue through static spin dephasing (gradient-echo sequences) and diffusion (gradient-echo and spin-echo sequences).

As shown by the FIGS. 2B, 2C, 3, in the presence of such local gradients the measured $ADC_{MPG}$ can be artifactually decreased when using usual Mono-Polar diffusion MRI sequences (see also Does et al., 1999; Kennan et al., 1995; Zhong et al., 1991; Kiselev, et al., 2004). As shown by the FIGS. 2B, 2C, this effect results from the presence of cross-terms between the local background gradients induced and the applied diffusion-encoding pulsed gradients. In the first extreme configuration as illustrated in FIG. 2B, the local background gradients induced by iron, the background gradients induced by other sources $G_{background}$, and the applied gradients are collinear, whereas in the second extreme configuration as illustrated in FIG. 2C the local background gradients induced by iron and the background gradients induced by other sources $G_{background}$ are anti-linear to applied diffusion gradients.

This ADC decrease may appear counterintuitive, but is well explained by the nonlinear relationship between the diffusion signal attenuation with the b value as shown in the FIG. 3. Negative cross-terms contribute more to increase the signal level (decrease in local effective $b^-_{eff}$ value) than positive cross-terms contribute to decrease the signal level (increase in local effective $b^+_{eff}$ values). As the distribution of negative and positive cross-terms is approximately equal, this asymmetry in the effect on the signal level results in an overall $b_{eff}$ decreased effective b value, or, in other hands, an artifactually decreased value for the ADC, which we call $ADC_{MPG}$. The effect can be quantified by a iron induced local gradient factor, $\xi_{Fe}$, to the b value, which depends on the measurement (diffusion) time and the variance of the local gradients (Zhong et al., 1991), and increases with the iron particle intrinsic relaxivity and concentration, [Fe], so that the diffusion signal attenuation, S/So, with the b values becomes:

$S/So = \exp\{-b(1-\xi_{Fe}).ADC\} \equiv \exp\{-b.ADC_{MPG}\}$ (Equation #3)

with $ADC_{MPG} = (1-\xi_{Fe}).ADC$, $S_0$ being the signal at b=0.

In other words, ignoring iron effect, fitting of diffusion MRI data with the equation #3 would lead to $ADC_{MPG}$ with $ADC_{MPG} < ADC$.

According to FIG. 4A an example of Bipolar Pulse-diffusion field Gradient Spin-Echo sequence is shown. The BPG is a twice refocused spin-echo sequence allowing any diffusion gradients lengths such that the time between the two refocusing pulses is equal to TE/2, and the phasing and re-phasing due to the diffusion gradients are equal, TE designating the echo time. Here, the diffusion gradient pulses have a same duration.

When using a Bipolar Gradient Pulse (BPG) or any second sequence as defined in the paper cited here above of Hong X. et al., the effect of cross-terms disappears, (which is translated into the equation #3 by setting $\xi$ to 0) so that the ADC is correctly estimated as $ADC_{MPG}$. Bulk Magnetic Susceptibility related effects on relaxivity R2* are included in So and are not affecting $ADC_{BPG}$ or $ADC_{MPG}$ which are estimated as independent parameters in Equation #3.

As shown in the FIGS. 4B-4C and FIGS. 4D-4E that correspond to high cross-terms configurations, the cross-terms effects between the local gradients and the applied gradients are removed by using a bipolar PGSE sequence, so that $\xi_{Fe} = 0$. Thus $ADC_{BPG} = ADC$.

The iron related local gradient parameter can be obtained as:

$\xi_{Fe} = 1 - ADC_{MPG}/ADC_{BPG}$ (Equation #4)

It should be noted that the Equation #3 corresponds to a model function, f, that is mono-exponential and is expressed by the first model function $f_1(x)$ as:

$f_1(b.ADC) = \exp(-b.ADC)$ (Equation #5)

However by using such a first model, the water diffusion is described by a single ADC which does not adequately reflect water diffusion behavior in all the tissues. Diffusion in most tissues, in particular brain tissues, is not free and therefore molecular displacements do not follow a Gaussian distribution. As a result, signal attenuation plots of ln(S) versus b value, ln designating the Neper logarithm function, are curved and do not follow a straight line, even in the absence of BMS effects, as would be expected from Equation #5. Several models have been proposed to explain this curvature effect.

One empiric way to describe this curvature (and the deviation from Gaussian diffusion) is to develop the signal attenuation as a cumulant expansion (Taylor series) (Chabert et al., 2004; Jensen and Helpern, 2010). The equation #3 then becomes by limiting its development to the second order term:

$S/So = \exp[-b(1-\xi_{Fe}).ADC + K.(b(1-\xi_{Fe}).ADC)^2/6]$ $S/So \equiv \exp[-b.ADC_{MPG} + K.(b.ADC_{MPG})^2/6]$ (equation #6)

with again $ADC_{MPG} = (1-\xi_{Fe}).ADC$, where ADC is now the intrinsic diffusion coefficient when $\xi_{Fe}$ reaches 0 and K is called kurtosis (related to the $4^{th}$ moment of the molecular displacement in the narrow gradient pulse regime). ADC can be directly estimated from Equation #6 using a BPG sequence by setting $\xi_{Fe}$ equal to 0, so that the iron related local gradient parameter can be obtained again from Equation 4.

It should be noted that the Equation #6 corresponds to a model function that is a Kurtosis function, and is expressed by a second model function $f_2(x)$ defined as:

$$f_2(x) = \exp\left(-b.ADC + K \cdot \frac{(b.ADC)^2}{6}\right)$$ (Equation #7)

where K is the kurtosis related to a $4^{th}$ moment of the molecular displacement in a narrow gradient pulse regime.

In order to estimate the first Apparent Diffusion Coefficient $ADC_{MPG}$ with the MPG sequence and the second Apparent Diffusion Coefficient $ADC_{BPG}$ with the BPG sequence, the MRI images are quantitatively processed using fitting algorithms which provide estimate of parameters according to a given non-linear signal model as for example a model from the diffusion MRI described by the equations #5 and #7. As a first approach the fitting of the signal data with the MRI diffusion model uses the standard iterative fitting search approach, as for example, the Levenberg-Marquardt algorithm.

As a second approach, the parameters of the MRI diffusion model are derived by comparing the raw MRI signal data acquired at all b values with those of a database of simulated signals built once-for-all using an exhaustive set of parameter combinations. This second approach is less sensitive to noise, has a greater stability and avoids the local minima resulting in parameter estimates which are somewhat far from the true values and may depend on the choice of initial parameter values which are required to launch the fitting process.

As a variant and in order to increase robustness, parameters $ADC_{BPG}$ and K are firstly estimated using BPG data, then $ADC_{MPG}$ is estimated using MPG data, fixing K to the value obtained with the BPG data. Such parameters may be estimated in the selected ROIs, leading to $\xi_{Fe}$, but also on a voxel-by-voxel basis to get parametric maps of $\xi_{Fe}$.

Figure 5:
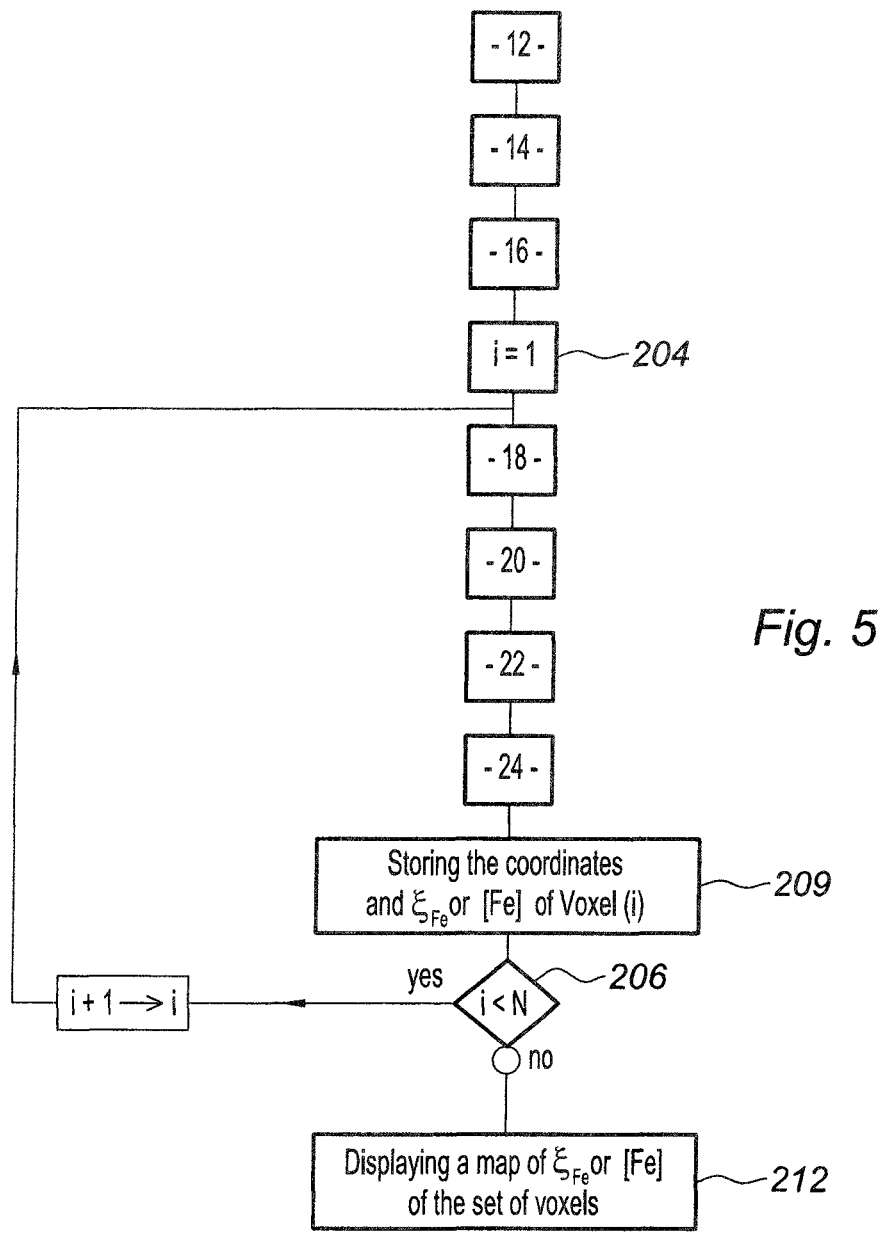
FIG. 5 is a flow chart of a variant of the method of FIG. 1 wherein a map of the iron concentrations of a predetermined set of voxels is built.

As a particular case of the first main embodiment of the general method described in the FIG. 1 and as illustrated in the FIG. 5, a method 202 for quantifying iron deposits in tissues comprises the same steps 12, 14, 16, 18, 20, 22, 22, 24 of the method 2, and comprises further steps 204, 206, 208 of a loop for implementing the determination of the iron concentration on a voxel or pixel basis over a set of voxels or pixels of a predetermined ROI, and comprises a further step for determining a two-dimensional map or a three-dimensional map of the iron density or iron quantities deposited in the observed tissue. As an example, the step 204 is a step for initializing a counter index i, wherein a value of the index i is assigned to one voxel or pixel of the set. In, the step 206, after executing the steps 20, 22, 24 for the voxel or pixel identified by the current index i, the value of the current index is compared to the total number N of the voxels or pixels of the set to be mapped. If the index i is lower than N the value of the index is incremented by one unity in the step 208, and the steps 20, 22, 24 are again executed with the updated value of the index i. If the in index i is equal to N, then the step 212 is executed. From the geometrical coordinates of the voxels of the set and their calculated correspondent iron concentrations (previously stored during of the step 24), a map of the iron concentrations is built concerning the ROI. As an example the map is a colored map whereon the different levels of iron concentration are encoded by different colors.

Figure 6:
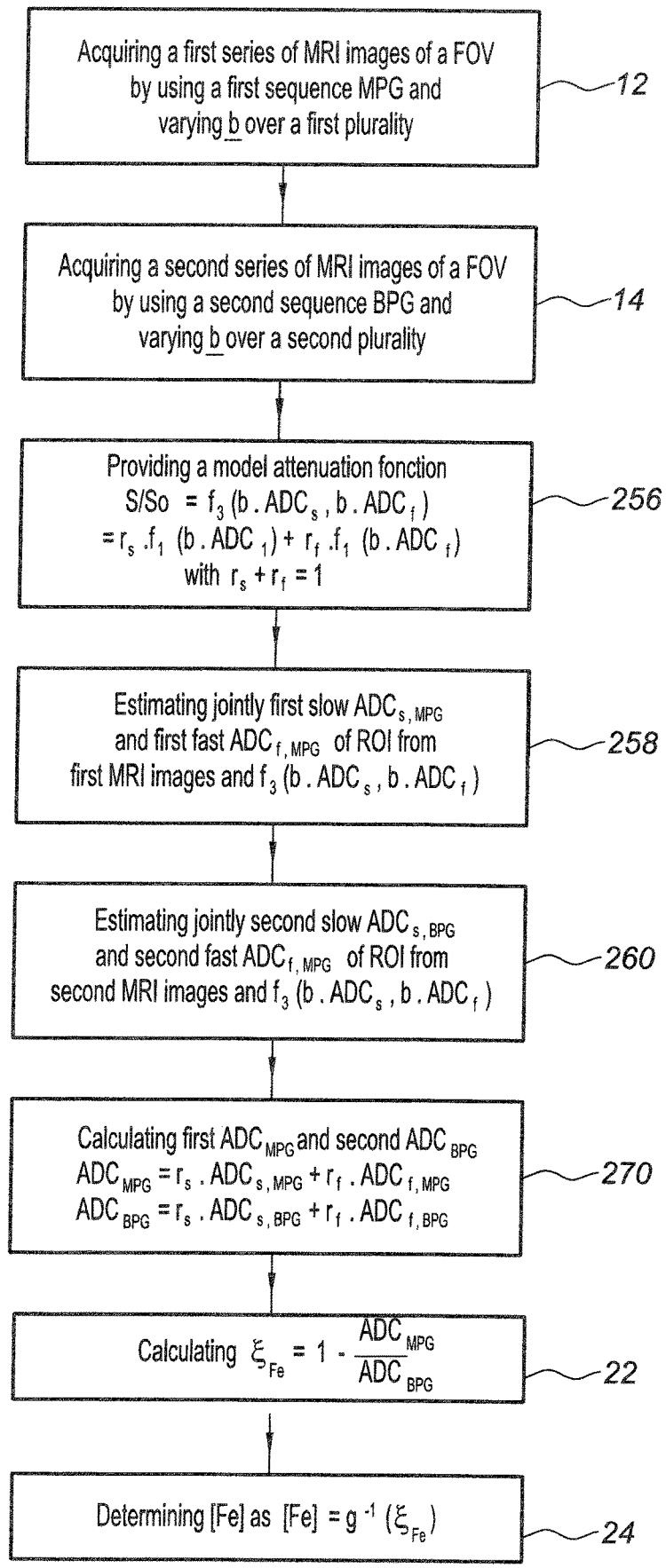
FIG. 6 is a flow chart of a method according to a second main embodiment of the invention for quantifying iron deposits in tissues.

As shown in the FIG. 6 and according to a second main embodiment of the invention, a method for quantifying iron deposits in tissues using diffusion-weighted Magnetic Resonance Imaging comprises a set 252 of steps 12, 14, 256, 258, 260, 270, 22, 24 wherein the function $f_1$ is applied to two water pools present in the tissue, resulting in a biexponential model, such as the model described in the paper of Niendorf T et al. [Niendorf T et al., 1996].

The first and second steps 12, 14 for acquiring a first series and a second series of MRI images of a Field Of View (FOV) of a biological tissue are the same as ones described in FIG. 1.

In a third step 256, the bi-exponential attenuation model function $f_3(b.ADC_s, b.ADC_f)$ of the diffusion MRI attenuated signal $S/S_0$ is provided and is expressed as:

$$f_3(b.ADC_s, b.ADC_f) = r_s f_1(-b.ADC_s) + r_f f_1 \exp(-b.ADC_f)$$  (equation #8)

wherein $ADC_s$ and $ADC_f$ designate respectively a slow apparent model diffusion coefficient concerning a slow diffusing water pool and a fast apparent model diffusion coefficient concerning a fast diffusing water pool, b designates the programmed gradient attenuation factor b used, $r_s$ and $r_f$ are respectively the relative fraction of the slow diffusing water pool and the relative fraction of the fast diffusing water pool with $r_s + r_f = 1$.

Then, after executing the first, second and third steps 12, 14, 256, on a one-per-one voxel basis or on a predetermined Region Of Interest (ROI) including a set of voxels, the steps referenced as 258, 260, 270, 22, 24 and described here below are executed.

In the fourth step 258 a first slow apparent diffusion coefficient $ADC_{s,MPG}$ and a first fast apparent diffusion coefficient $ADC_{f,MPG}$ are jointly estimated by fitting the MRI images acquired by using the MPG sequence and the first plurality of programmed gradient attenuation factors b with the model function $f_3(b.ADC_s, b.ADC_f)$.

In the fifth step 260, a second slow apparent diffusion coefficient $ADC_{s,BPG}$ and a second fast apparent diffusion coefficient $ADC_{f,BPG}$ are jointly estimated by fitting the MRI images acquired by using the BPG sequence and the second plurality of programmed gradient attenuation factors b with the model function $f_3(b.ADC_s, b.ADC_f)$.

Then, in the sixth step 270, a first apparent diffusion coefficient $ADC_{MPG}$ and a second apparent diffusion coefficient $ADC_{BPG}$ are calculated according to the relationships:

$$ADC_{MPG} = r_s.ADC_{s,MPG} + r_f.ADC_{f,MPG}, \text{ and}$$

$$ADC_{BPG} = r_s.ADC_{s,MPG} + r_f.ADC_{f,BPG},$$  (equations #9)

Then, the same step 22 as one described in FIG. 1, wherein an iron induced local gradient factor $\xi_{Fe}$ is calculated from the calculated values of the first apparent diffusion coefficient $ADC_{MPG}$ and the second apparent diffusion coefficient $ADC_{BPG}$ through the relationship:

$$\xi_{Fe} = 1 - \frac{ADC_{MPG}}{ADC_{BPG}}.$$

If necessary in the same step as the 24 as one described in FIG. 1, the concentration [Fe] and/or the amount of iron stored in the ROI or each voxel of the tissue is determined from the calculated iron induced local gradient factor $\xi_{Fe}$ through a predetermined monotonic conversion function $g^{-1}(\xi_{Fe})$.

The second main embodiment of the invention can be generalized by using any attenuation model function of the diffusion MRI attenuated signal $S/S_0$ representative of the observed tissue, $f_{n,j}(b.ADC_1, \ldots, b.ADC_n)$, which is expressed as:

$$f_{n,j}(b \cdot ADC_1, \ldots, b \cdot ADC_n) = \sum_{i=1}^{n} r_i \cdot f_j(b \cdot ADC_i),$$  (equation #10)

wherein n designates the total number of diffusing water pools and is higher than or equal to 2,
i is an index assigned to a diffusing water pool varying from 1 to n,
j is an integer equal to 1 or 2 with $-f_1(b.ADC_i)$ being the mono-exponential function and $f_2(b.ADC_i)$ being the Kurtosis function as defined here above, $ADC_1, \ldots, ADC_n$ are the model apparent model diffusion coefficients corresponding to different diffusing water pools, and $r_1, \ldots, r_n$ are relative fractions corresponding to the different diffusing water pools with $$\sum_{i=1}^{n} r_i = 1.$$

In such a case, on a one-per-one voxel basis or on a predetermined Region Of Interest (ROI) including a set of voxels:

apparent diffusion coefficients $ADC_{i,MPG}$ of a first set are jointly estimated by fitting the MRI images acquired by using the MPG sequence and the first plurality of programmed gradient attenuation factors b with the model function $f_{n,j}(b.ADC_1, \ldots, b.ADC_n)$;

apparent diffusion coefficients $ADC_{i,BPG}$ of a second set are jointly estimated by fitting the MRI images acquired by using the BPG sequence and the second plurality of programmed gradient attenuation factors b with the model function $f_{n,j}(b.ADC_1, \ldots, b.ADC_n)$;

a first apparent diffusion coefficient $ADC_{MPG}$ and a second apparent diffusion coefficient $ADC_{BPG}$ are calculated according to the following relationships:

$$ADC_{MPG} = \sum_{i=1}^{n} r_i \cdot ADC_{i,MPG}, \text{ and}$$  (equation #11)

$$ADC_{BPG} = \sum_{i=1}^{n} r_i \cdot ADC_{i,BPG}.$$

Then, an iron induced local gradient factor $\xi_{Fe}$ from the calculated values of the first apparent diffusion coefficient $ADC_{MPG}$ and the second apparent diffusion coefficient $ADC_{BPG}$ through the relationship:

$$\xi_{Fe} = 1 - \frac{ADC_{MPG}}{ADC_{BPG}}.$$

According to FIG. 7, an apparatus 302 for quantifying iron deposits in tissues comprises a magnetic resonance imaging scanner 304 to operate diffusion-weighted magnetic resonance imaging with a high spatial resolution and accuracy and a means 306 for controlling the scanner 304 and processing the MRI imaging data acquired by the scanner.

The magnetic resonance imaging scanner 304 is configured for:

generating a MPG sequence as a mono-polar Pulse-diffusion Gradient Spin-Echo (PGSE) sequence, and varying a programmed gradient attenuation factor b over a first plurality of values, the programmed gradient attenuation factors b depending only on the set of the gradients pulses; and generating a BPG sequence as a cross-term-free pulse diffusion gradient spin-echo sequence having a similar diffusion time as the first sequence and varying a programmed gradient attenuation factor b over a second plurality of values; and acquiring a first series of MRI images of a Field Of View (FOV) of a biological tissue by using the second sequence for the different programmed gradient attenuation factor b values of the first plurality;

acquiring a second series of MRI images of the same Field Of View (FOV) of the biological tissue by using the second sequence for the different programmed gradient attenuation factor b values of the second plurality.

The means 306 for controlling the scanner and processing the imaging data acquired by the scanner comprises a means 308 for storing an attenuation model of the diffusion MRI attenuated signal representative of the observed tissue and a processing means 310.

The diffusion MRI attenuated signal representative of the observed tissue is expressed in the same way as described for FIG. 1.

The processing means 310 is configured for, on a one-per-one voxel basis or on a predetermined Region Of Interest (ROI) including a set of voxels:

estimating a first apparent diffusion coefficient $ADC_{MPG}$ by fitting the MRI images acquired by using the first sequence and the first plurality of programmed gradient attenuation factors with the model function f(b.ADC);

estimating a second apparent diffusion coefficient $ADC_{BPG}$ by fitting the MRI images acquired by using the second sequence and the second plurality of programmed gradient attenuation factors, with the model function f(b.ADC);

calculating a iron induced local gradient factor $\xi_{Fe}$ from the estimated values of the first apparent diffusion coefficient $ADC_{MPG}$ and the second apparent diffusion coefficient $ADC_{BPG}$ through the relationship $$\xi_{Fe} = 1 - \frac{ADC_{MPG}}{ADC_{BPG}},$$

which provides with information on the relative iron content between tissues and/or conditions (e.g. normal or disease);

if necessary, determining the absolute concentration [Fe] and/or the amount of iron stored in the ROI or each voxel of the tissue from the calculated correction factor $\xi_{Fe}$ through a predetermined conversion function $g^{-1}$ ($\xi_{Fe}$).

As a variant, the means 308 for storing an attenuation model of the diffusion MRI attenuated signal representative of the observed tissue and the processing means 310 are respectively configured to store the bi-exponential attenuation model used by the method 252 of FIG. 6 or any model using a $f_{n,j}$ model function, and to process the processing steps 258, 260, 270, 22, 24 as described in FIG. 6, or process similar steps suited to the processing using a $f_{n,j}$ model function.

A computer software comprises a set of instructions that, after being loaded in the means 306 for controlling and process the data, are executed to carry out partially or fully the steps as described in FIG. 1, or FIG. 5 or FIG. 6.

It should be noted that the steps for processing the MRI data can be carried out on a standalone console different from the MRI scanner console through a dedicated computer software.

Here below some results are presented concerning MRI measurements that have been done in the brain of four non-human primates (Rhesus monkeys) of various ages designated respectively by the letters B, Y, T, N, in order to validate the method of the invention and to establish a calibration for determining the conversion function $g^{-1}$, in the case of iron measurements in the brain tissues of monkeys.

The materials and methods used more specifically to obtain the MRI measurements are described here below.

Concerning MRI acquisition, series of images were acquired using a whole-body 33 T MRI scanner (Siemens, Erlangen, Germany) using a 4 channel phased-array coil with a diffusion-weighted echo-planar imaging (EPI) sequence. The MPG sequence parameters were: TE/TR=89/3000 ms, FOV=128 mm, matrix=64×64, 15 slices of 2 mm thickness in the axial direction, b=0, 200, 600, 1000, 1400, 1800, 2200, 2600, 3000 s/mm². The same parameters were used for the BPG sequence (twice refocused spin-echo sequence) except for the bipolar gradient pulses (Song et al., 1999; Reese et al., 2003). All BPG pulses had an equal duration (9.4 ms separated by a 9.4 ms interval) to fully cancel cross-terms and the 2 gradient pairs were separated by a 16 ms interval. For the MPG and BPG sequences gradient pulses were applied simultaneously on X, Y and Z axes (gradient vector=[1, 1, 1]), as diffusion anisotropy effects were not relevant to this study. Each acquisition was repeated 6 times for averaging in order to increase signal to noise ratio (SNR). A 3D MPRAGE (TR/TE=2200/3.2 ms, FOV=154 mm, matrix=192×192, 104 slices of 0.8 mm thickness in the sagittal direction, resulting in 0.8 mm isotropic resolution) was also used to obtain T1-weighted reference anatomical images.

The MRI images have been quantitatively processed using a fitting algorithm which provides estimate of parameters according to a Kurtosis function model, here the estimated parameters being the kurtosis K, the first Apparent Diffusion Coefficient $ADC_{MPG}$ and the second Apparent Diffusion Coefficient $ADC_{BPG}$.

The FIGS. 8a and 8b from the left to the right illustrate respectively the ROI locations on a phantom and in the monkey B for the Substantia Nigra (SN), the Globus Pallidus (GP), the thalamus and the cortex.

The overall acquisition scheme of the method has been firstly validated using a phantom at room temperature (20-22° C.). The phantom (2-cm-diameter plastic syringe) was filled with cyclohexane (Sigma-Aldrich Chimie, Lyon, France). Regions of interest (ROIs) for measurements were placed on five slices in the center of the syringe as shown in FIG. 8a.

MRI measurements of the endogenous iron concentration in the cortex and basal ganglia of the Rhesus monkeys B, Y, T, N as shown in FIG. 10 have been compared with estimated the endogenous iron concentration in the cortex and basal ganglia (Substantia Nigra and Globus Pallidus) from a model built by Hardy P A et al. In this model the iron concentration has been estimated in Substantia Nigra (SN) and the Globus Pallidus (GP) using a relationship between age and iron concentration established from histological measurements in rhesus monkeys (Hardy P A, et al., 2005): $[Fe]_{SN}=11.1 \times age$ (years)$-18.5$; $[Fe]_{GP}=13.1 \times age$ (years)$+106$, where [Fe] is the iron concentration (μg/g-ww). The relationship between $\xi_{Fe}$ and the estimated iron concentration [Fe] was tested using a linear regression performed using MedCalc (MedCalc Software, Ostend, Belgium) and shows that a linear model can be used for describing the evolution of [Fe] versus $\xi_{Fe}$.

As shown in FIG. 11, the overall relationship (taking into account SN and GP regions from all animals) between $\xi_{Fe}$ and the estimated iron concentration is clearly linear, with [Fe] [mg/g-ww]$=5197.3 \times \xi_{Fe}-371.5$ ($R^2=0.7949$, $p=0.003$), whereas there were no significant correlations between $\xi_{Fe}$ and D and K ($R^2=0.04675$ and $0.006196$, $p=0.607$ and $0.853$, respectively).

Diffusion MRI has been shown here above to be exquisitely sensitive to subtle changes occurring in tissue microstructure, especially in the brain (Le Bihan, et al., 2012). According to the method of invention the diffusion MRI can be used to quantify iron deposits at concentrations apparently as low as a few tens of μg/g-ww. The possibility to estimate of the iron load in tissues, especially brain basal ganglia, noninvasively is an important achievement.

Diffusion MRI is sensitive to the presence of iron deposit in tissues and can be used to quantify iron and get maps of iron content in the brain tissue with good accuracy. Such a method will benefit clinical investigations on the effect of systemic iron overload in the liver or in specific tissues, such as the brain where iron deposits have been shown to induce neurodegenerative disorders, such as Parkinson's disease.

REFERENCES

1. Antonini A1, Leenders K L, Meier D, Oertel W H, Boesiger P, Anliker M. T2 relaxation time in patients with Parkinson's disease. Neurology. 1993; 43:697-700.
2. Aquino D, Bizzi A, Grisoli M, Garavaglia B, Bruzzone M G, Nardocci N, Savoiardo M, Chiapparini L. Age-related iron deposition in the basal ganglia: quantitative analysis in healthy subjects. Radiology. 2009; 252:165-72.
3. Berg D, Youdim M B. Role of iron in neurodegenerative disorders. Top Magn Reson Imaging. 2006; 17:5-17.
4. Brass S D, Chen N K, Mulkern R V, Bakshi R. Magnetic resonance imaging of iron deposition in neurological disorders. Top Magn Reson Imaging. 2006; 17:31-40.
5. Chabert, S., Mecca, C. C., Le Bihan, D. J., 2004. Relevance of the information about the diffusion distribution in invo given by kurtosis in q-space imaging. Proceedings, 12$^{th}$ ISMRM annual meeting, p. 1238.
6. Clark C A, Le Bihan D. Water diffusion compartmentation and anisotropy at high b values in the human brain. Magn Reson Med. 2000; 44:852-9.
7. Deistung A, Schäfer A, Schweser F, Biedermann U, Turner R, Reichenbach J R. Toward in vivo histology: a comparison of quantitative susceptibility mapping (QSM) with magnitude-, phase-, and R2*-imaging at ultra-high magnetic field strength. Neuroimage. 2013; 65:299-314.
8. Does M D, Zhong J, Gore J C. In vivo measurement of ADC change due to intravascular susceptibility variation. Magn Reson Med. 1999; 41:236-40.
9. Y Gandon, D Olivié, D Guyader, C Aube, F Oberti, V Sebille, Y Deugnier. Non-invasive assessment of hepatic iron stores by MRI. THE LANCET•Vol 363•Jan. 31, 2004.
10. Gorell J M1, Ordidge R J, Brown G G, Deniau J C, Buderer N M, Helpern J A. Increased iron-related MRI contrast in the substantia nigra in Parkinson's disease. Neurology. 1995; 45:1138-43.
11. Graham J M, Paley M N, Grünewald R A, Hoggard N, Griffiths P D. Brain iron deposition in Parkinson's disease imaged using the PRIME magnetic resonance sequence. Brain. 2000; 123:2423-31.
12. Griffiths P D, Crossman A R. Distribution of iron in the basal ganglia and neocortex in postmortem tissue in Parkinson's disease and Alzheimer's disease. Dementia. 1993; 4:61-5.
13. Griffiths P D, Dobson B R, Jones G R, Clarke D T. Iron in the basal ganglia in Parkinson's disease. An in vitro study using extended X-ray absorption fine structure and cryo-electron microscopy. Brain. 1999; 122 (Pt 4):667-73.
14. Haacke E M, Cheng N Y, House M J, Liu Q, Neelavalli J, Ogg R J, Khan A, Ayaz M, Kirsch W, Obenaus A. Imaging iron stores in the brain using magnetic resonance imaging. Magn Reson Imaging. 2005; 23:1-25. Review.
15. Hallgren B, Sourander P. The effect of age on the non-haemin iron in the human brain. J Neurochem 1958; 3:41-51.
16. Hardy P A, Gash D, Yokel R, Andersen A, Ai Y, Zhang Z. Correlation of R2 with total iron concentration in the brains of rhesus monkeys. J Magn Reson Imaging. 2005; 21:118-27.
17. Hong X, DIXON W. T., "Measuring Diffusion in Inhomogeneous Systems in Imaging Mode Using Antisymmetric Sensitizing Gradients", Journal of Magnetic Resonance 99, 561-570, 1992.
18. Jensen, J H., Helpern, J A. MRI quantification of non-Gaussian water diffusion bykurtosis analysis. NMR Biomed 2010; 59:698-710.
19. Kennan et al. 1995
20. Kiselev V G. Effect of magnetic field gradients induced by microvasculature on NMR measurements of molecular self-diffusion in biological tissues. J Magn Reson 2004; 170, 228-235.
21. Milton W J, Atlas S W, Lexa F J, Mozley P D, Gur R E. Deep gray matter hypointensity patterns with aging in healthy adults: M R imaging at 1.5 T. Radiology. 1991; 181:715-9.
22. Niendorf T, Dijkhuizen R M, Norris D G, van Lookeren Campagne M, Nicolay K, Biexponential diffusion attenuation in various states of brain tissue: implications for diffusion-weighted imaging, Magn. Reson. Med. 1996; 36:847-857.
23. Péran P, Cherubini A, Luccichenti G, Hagberg G, Démonet J F, Rascol O, Celsis P, Caltagirone C, Spalletta G, Sabatini U. Volume and iron content in basal ganglia and thalamus. Hum Brain Mapp 2009; 30:2667-75.

24. Reese T G, Heid O, Weisskoff R M, Wedeen V J. Reduction of eddy-current-induced distortion in diffusion MRI using a twice-refocused spin echo. Magn Reson Med. 2003; 49:177-82.
25. St. Pierre T G, Clark P R, Chua-anusorn W, Fleming A J, Jeffrey G P, Olynyk J K, Pootrakul P, Robins E, and Lindeman R. Noninvasive measurement and imaging of liver iron concentrations using proton magnetic resonance. BLOOD, 15 Jan. 2005 VOLUME 105, NUMBER 2.
26. Schenker C, Meier D, Wichmann W, Boesiger P, Valavanis A. Age distribution and iron dependency of the T2 relaxation time in the globus pallidus and putamen. Neuroradiology. 1993; 35:119-24.
27. Sedlacik J, Boelmans K, Löbel U, Holst B, Siemonsen S, Fiehler J. Reversible, irreversible and effective transverse relaxation rates in normal aging brain at 3 T. Neuroimage. 2014; 84:1032-41.
28. Wallis L I, Paley M N, Graham J M, Grünewald R A, Wignall E L, Joy H M, Griffiths P D. MRI assessment of basal ganglia iron deposition in Parkinson's disease. J Magn Reson Imaging. 2008; 28:1061-7. doi: 10.1002/jmri.21563.
29. Zhong J H, Kennan R P, Gore J C. Effects of Susceptibility Variations on NMR Measurements of Diffusion. J Magn Reson 1991; 95:267-280.
30. Zhong J H, Kennan R P, Fulbright R K, Gore J C. Quantification of intravascular and extravascular contributions to BOLD effects induced by alteration in oxygenation or intravascular contrast agents. Magn Reson Med. 1998; 40:526-36.

The invention claimed is:

1. A method for quantifying iron deposits in tissues using diffusion-weighted Magnetic Resonance Imaging (MRI) with a high accuracy, comprising the following steps:
   step (12): acquiring a first series of MRI images of a Field Of View (FOV) of a biological tissue by using a MonoPolar pulse-diffusion Gradient (MPG) sequence as a MonoPolar pulse-diffusion Gradient Spin-Echo sequence (PGSE), and by varying a programmed gradient attenuation factor b over a first plurality of values, the programmed gradient attenuation factor depending only on the set of the diffusion gradient pulses of the first sequence;
   step (14): acquiring a second series of MM images of the same Field of View FOV of the biological tissue by using as a BiPolar pulse-diffusion Gradient (BPG) sequence, a cross-term-free pulse-diffusion gradient spin echo sequence having a similar diffusion time as the MPG sequence, this BPG sequence having its diffusion-sensitizing gradients and RF pulses arranged so that the cross terms between the local magnetic field gradients induced by iron and the gradient pulses within the BPG sequence are equal to zero at the echo time TE period, and by varying a programmed gradient attenuation factor b over a second plurality of values, the programmed gradient attenuation factor depending only on the set of the diffusion gradient pulses of the BPG sequence;
   step (16): providing an attenuation model of the diffusion MM attenuated signal $S/S_0$ representative of the observed tissue expressed as a model function f(x) depending on a variable x equal to the product of an apparent model diffusion coefficient ADC and the programmed gradient attenuation factor b used; on a one-per-one voxel basis or on a predetermined Region Of Interest (ROI) including a set of voxels,
   step (18): estimating a first apparent diffusion coefficient $ADC_{MPG}$ by fitting the MRI images acquired by using the MPG sequence and the first plurality of programmed gradient attenuation factors b with the model function f(b.ADC);
   step (20): estimating a second apparent diffusion coefficient ADCBPG by fitting the MM images acquired by using the BPG sequence and the second plurality of programmed gradient attenuation factors b with the model function f(b.ADC);
   step (22): calculating a local gradient factor $\xi_{Fe}$ quantitatively reflecting the iron load in each voxel or ROI from the estimated values of the first apparent diffusion coefficient ADCMPG and the second apparent diffusion coefficient ADCBPG through the relationship:

$$\xi_{Fe} = 1 - \frac{ADC_{MPG}}{ADC_{BPG}}.$$

2. The method for quantifying iron deposits in tissues according to claim 1, wherein the concentration [Fe] and/or the amount of iron stored in the ROI or each voxel of the tissue is determined from the calculated iron induced local gradient factor $\xi_{Fe}$ through a predetermined monotonic conversion function $g^{-1}(\xi_{Fe})$ of the iron induced local gradient factor $\xi_{Fe}$ giving the absolute quantification of iron.

3. The method for quantifying iron deposits in tissues according to claim 2, wherein the conversion function $g^{-1}(\xi_{Fe})$ is a linear function or a portion of a quadratic function.

4. The method for quantifying iron deposits in tissues according to claim 1, wherein the BPG sequence is a twice refocused spin-echo sequence allowing any diffusion gradients lengths such that the time between the two refocusing pulses is equal to TE/2, and the phasing and re-phasing due to the diffusion gradients are equal, TE designating the echo time.

5. The method for quantifying iron deposits in tissues according to claim 1, wherein the mono-polar Pulse-diffusion field Gradient Spin-Echo sequence is a singly-refocused Stejkal-Tanner spin-echo sequence.

6. The method for quantifying iron deposits in tissues according to claim 1, comprising further a step of determining a two-dimensional map or a three-dimensional map of the iron induced iron induced local gradient factor $\xi_{Fe}$ or the iron concentration [Fe] or iron quantities deposited in the observed tissue when the estimation steps are carried out on a one per one voxel basis.

7. The method for quantifying iron deposits in tissues according to claim 1, wherein the model function f(x) is mono-exponential and is expressed by a first model function $f_1(x)$ as:

$$f_1(b.ADC)) = \exp(-b.ADC).$$

8. The method for quantifying iron deposits in tissues according to claim 1, wherein the model function f(x) is a Kurtosis function, and is expressed by a second model function $f_2(x)$ as:

$$f_2(b.ADC) = \exp(-b.ADC + K.(b.ADC)^2/6)$$

where K is the kurtosis related to a $4^{th}$ moment of the molecular displacement in a narrow gradient pulse regime.

9. The method for quantifying iron deposits in tissues according to claim 8, wherein the observed tissue is a tissue of the set consisting of the brain tissues, liver tissues, heart joints tissues.

10. The method for quantifying iron deposits in tissues according to claim 1, wherein the estimation of the first apparent diffusion coefficient ADCMPG and the estimation of the second apparent diffusion coefficient ADCBPG are carried out by comparing the raw MRI signal data with a database of simulated signals built once-for-all using an exhaustive set of parameters combinations, the parameters being those of the model function f(x) and including at least the programmed gradient attenuation factor b and the apparent model diffusion coefficient ADC.

11. A method for quantifying iron deposits in tissues using diffusion-weighted Magnetic Resonance Imaging (MRI) with a high accuracy, comprising the following steps:
   step (12): acquiring a first series of MRI images of a Field Of View (FOV) of a biological tissue by using a MonoPolar pulse-diffusion Gradient (MPG) sequence as a MonoPolar pulse-diffusion Gradient Spin-Echo sequence (PGSE), and by varying a programmed gradient attenuation factor b over a first plurality of values, the programmed gradient attenuation factor depending only on the set of the diffusion gradient pulses of the first sequence;
   step (14): acquiring a second series of MM images of the same Field of View FOV of the biological tissue by using as a BiPolar pulse-diffusion Gradient (BPG) sequence a cross-term-free pulse-diffusion gradient spin echo sequence having a similar diffusion time as the MPG sequence, and by varying a programmed gradient attenuation factor b over a second plurality of values, the programmed gradient attenuation factor depending only on the set of the diffusion gradient pulses of the BPG sequence;
   step (256): providing an attenuation model of the diffusion MRI attenuated signal $S/S_0$ representative of the observed tissue, $f_{n,j}(b.ADC_1, \ldots, b.ADC_n)$ which can be expressed as:

$$f_{n,j}(b \cdot ADC_1, \ldots, b \cdot ADC_n) = \sum_{i=1}^{n} r_i \cdot f_j(b \cdot ADC_i),$$

wherein
   n designates the total number of the diffusing water pools and is higher than or equal to 2,
   i is an index assigned to a diffusing water pool varying from 1 to n,
   j is an integer equal to 1 or 2 with $f_1(b.ADC)$ being the mono-exponential function as defined in claim 7 and $f_2(b.ADC_i)$ being the Kurtosis function as defined in claim 8,
   $ADC_1, \ldots, ADC_n$ are the model apparent model diffusion coefficients corresponding to different diffusing water pools, and $r_1, \ldots, r_n$ are the relative fractions corresponding to the different diffusing water pools with $$\sum_{i=1}^{n} r_i = 1;$$

on a one-per-one voxel basis or on a predetermined Region Of Interest (ROI) including a set of voxels,
   step (258): estimating jointly a first set of apparent diffusion coefficient $ADC_{i,MPG}$ by fitting the MRI images acquired by using the MPG sequence and the first plurality of programmed gradient attenuation factors b with the model function $f_{n,j}(b.ADC_1, \ldots, b.ADC_n)$;
   step (260): estimating jointly a second set of apparent diffusion coefficient $ADC_{i,BPG}$ by fitting the MM images acquired by using the BPG sequence and the second plurality of programmed gradient attenuation factors b with the model function $f_{n,j}(b.ADC_1, \ldots, b.ADC_n)$;
   step (270): calculating a first apparent diffusion coefficient $ADC_{MPG}$ and a second apparent diffusion coefficient ADCBPG according to the relationships:

$$ADC_{MPG} = \sum_{i=1}^{n} r_i \cdot ADC_{i,MPG}, \text{ and}$$

$$ADC_{BPG} = \sum_{i=1}^{n} r_i \cdot ADC_{i,BPG},$$

step (22): calculating a local gradient factor $\xi_{Fe}$ quantitatively reflecting the iron load in each voxel or ROI from the calculated values of the first apparent diffusion coefficient $ADC_{MPG}$ and the second apparent diffusion coefficient ADCBPG through the relationship:

$$\xi_{Fe} = 1 - \frac{ADC_{MPG}}{ADC_{BPG}}.$$

12. The method for quantifying iron deposits in tissues according to claim 11, wherein the concentration [Fe] and/or the amount of iron stored in the ROI or each voxel of the tissue is determined from the calculated iron induced local gradient factor $\xi_{Fe}$ through a predetermined monotonic conversion function $g^{-1}(\xi_{Fe})$.

13. An apparatus for quantifying iron deposits in tissues comprising a magnetic resonance imaging scanner to operate diffusion-weighted magnetic resonance imaging with a high resolution and accuracy and a means for controlling the scanner and processing the imaging data acquired by the scanner;
   the magnetic resonance imaging scanner being configured for
     generating a MonoPolar pulse-diffusion Gradient (MPG) sequence as a Mono-Polar Pulse-diffusion Gradient Spin-Echo (PGSE) sequence, and varying a programmed gradient attenuation factor b over a first plurality of values, the programmed gradient attenuation factor b depending only on the set of the gradient pulses; and
     generating a Bipolar pulse-diffusion Gradient (BPG) sequence as a cross-term free pulse diffusion Gradient Spin-Echo sequence having a similar diffusion time as the MPG sequence, this BPG sequence having its diffusion-sensitizing gradients and RF pulses arranged so that the cross terms between the imaging gradient, the local gradient, the sensitizing gradient are equal to zero at the echo time TE period, and varying a programmed gradient attenuation factor b over a second plurality of values; and acquiring a first series of MM images of a Field Of View (FOV) of a biological tissue by using the MPG sequence for the different programmed gradient attenuation factor b values of the first plurality;

acquiring a second series of MRI images of the same Field Of View (FOV) of the biological tissue by using the BPG sequence for the different programmed gradient attenuation factor b values of the second plurality; and the means for controlling the scanner and processing the imaging data acquired by the scanner comprising a means for storing an attenuation model of the diffusion MRI attenuated signal $S/S_0$ representative of the observed tissue expressed as a model function f(x) depending on a variable x equal to the product of an apparent model diffusion coefficient ADC and the programmed gradient attenuation factor b used; and a processing means configured for, on a one-per-one voxel basis or on a predetermined Region Of Interest (ROI) including a set of voxels;

estimating a first apparent diffusion coefficient ADCMPG by fitting the MRI images acquired by using the MPG sequence and the first plurality of programmed gradient attenuation factors with the model function f(b.ADC);

estimating a second apparent diffusion coefficient ADCBPG by fitting the MRI images acquired by using the BPG sequence and the second plurality of programmed gradient attenuation factors, with the model function f(b.ADC);

calculating a local gradient factor $\xi_{Fe}$ quantitatively reflecting the iron load in each voxel or ROI from the estimated values of the first apparent diffusion coefficient ADCMPG and the second apparent diffusion coefficient ADCBPG through the relationship $$\xi_{Fe} = 1 - \frac{ADC_{MPG}}{ADC_{BPG}}.$$

14. The apparatus for quantifying iron deposits in tissues according to claim 13, wherein the means for storing a model stores at least one attenuation model function among a first model function $f_1$(b.ADC), a second model function $f_2$(b.ADC), the first model function $f_1$(x) being mono-exponential and being expressed as:

$f_1(b.\text{ADC})) = \exp(-b.\text{ADC})$ the second model function $f_2$(x) being a Kurtosis function and being expressed as:

$f_2(b.\text{ADC}) = \exp(-b.\text{ADC} + K.(b.\text{ADC})^2/6)$ where K is the kurtosis related to a $4^{th}$ moment of the molecular displacement in a narrow gradient pulse regime.

15. An apparatus for quantifying iron deposits in tissues comprising a magnetic resonance imaging scanner to operate diffusion-weighted magnetic resonance imaging with a high resolution and accuracy and a means for controlling the scanner and processing the imaging data acquired by the scanner;

the magnetic resonance imaging scanner being configured for generating a MPG sequence as a Mono-Polar Pulse-diffusion Gradient Spin-Echo (PGSE) sequence, and varying a programmed gradient attenuation factor b over a first plurality of values, the programmed gradient attenuation factor b depending only on the set of the gradient pulses; and generating a BPG sequence as a cross-term free pulse diffusion Gradient Spin-Echo sequence having a similar diffusion time as the MPG sequence, and varying a programmed gradient attenuation factor b over a second plurality of values; and acquiring a first series of MM images of a Field Of View (FOV) of a biological tissue by using the MPG sequence for the different programmed gradient attenuation factor b values of the first plurality;

acquiring a second series of MRI images of the same Field Of View (FOV) of the biological tissue by using the BPG sequence for the different programmed gradient attenuation factor b values of the second plurality; and the means for controlling the scanner and processing the imaging data acquired by the scanner comprising a means for storing an attenuation model of the diffusion MRI attenuated signal $S/S_0$ representative of the observed tissue, $f_{n,j}(b.\text{ADC}_1, \ldots, b.\text{ADC}_n)$ which is expressed as:

$$f_{n,j}(b \cdot ADC_1, \ldots, b \cdot ADC_n) = \sum_{i=1}^{n} r_i \cdot f_j(b \cdot ADC_i),$$

wherein n designates the total number of the diffusing water pools and is higher than or equal to 2, i is an index assigned to a diffusing water pool varying from 1 to n, j is an integer equal to 1 or 2 with $f_1$(b.$ADC_i$) being the mono-exponential function and $f_2$(b.$ADC_i$) being the Kurtosis function as defined in claim 14, $ADC_1, \ldots, ADC_n$ are the model apparent model diffusion coefficients corresponding to different diffusing water pools, and $r_1, \ldots, r_n$ are relative fractions corresponding to different pools with $$\sum_{i=1}^{n} r_i = 1;$$

and a processing means configured for, on a one-per-one voxel basis or on a predetermined Region Of Interest (ROI) including a set of voxels;

estimating jointly a first set of apparent diffusion coefficient $ADC_{i,MPG}$ by fitting the MRI images acquired by using the MPG sequence and the first plurality of programmed gradient attenuation factors b with the model function $f_{n,j}(b.\text{ADC}_1, \ldots, b.\text{ADC}_n)$;

estimating jointly a second set of apparent diffusion coefficient $ADC_{i,BPG}$ by fitting the MRI images acquired by using the BPG sequence and the second plurality of programmed gradient attenuation factors b with the model function $f_{n,j}(b.\text{ADC}_1, \ldots, b.\text{ADC}_n)$;

calculating a first apparent diffusion coefficient $ADC_{MPG}$ and a second apparent diffusion coefficient $ADC_{BPG}$ according to the relationships:

$$ADC_{MPG} = \sum_{i=1}^{n} r_i \cdot ADC_{i,MPG}, \text{ and}$$

$$ADC_{BPG} = \sum_{i=1}^{n} r_i \cdot ADC_{i,BPG};$$

calculating a local gradient factor $\xi_{Fe}$ quantitatively reflecting the iron load from the estimated values of the first apparent diffusion coefficient $ADC_{MPG}$ and the second apparent diffusion coefficient $ADC_{BPG}$ through the relationship $$\xi_{Fe} = 1 - \frac{ADC_{MPG}}{ADC_{BPG}}.$$

16. The apparatus for quantifying iron deposits in tissues according to claim 13, wherein the concentration [Fe] and/or the amount of iron stored in the ROI or each voxel of the tissue is determined from the calculated iron induced local gradient factor $\xi_{Fe}$ through a predetermined monotonic conversion function $g^{-1}(\xi_{Fe})$ of the iron induced local gradient factor $\xi_{Fe}$ giving the absolute quantification of iron.

17. The apparatus for quantifying iron deposits in tissues according to claim 13, wherein the processing means is configured for determining a two-dimensional map or a three-dimensional map of the iron induced local gradient factor $\xi_{Fe}$ or the iron concentration [Fe] or iron quantities deposited in the observed tissue when the estimation steps are carried out on a one per one voxel basis.

18. Computer software comprising a set of instructions stored in a means for controlling and processing data, the set of instructions being configured to carry out the steps of the method as defined in claim 1.

19. Computer software comprising a set of instructions stored in a stand-alone computer, the set of instruction being configured to carry out the method as defined in claim 1.

* * * * *